United States Patent
Nagata et al.

(10) Patent No.: US 6,403,785 B1
(45) Date of Patent: Jun. 11, 2002

(54) ISOLATED DNA MOLECULE ENCODING HUMAN TSC403

(75) Inventors: Masami Nagata, Tama; Kouichi Ozaki, Tokushima; Yoshikazu Shimada; Masato Horie, both of Naruto, all of (JP)

(73) Assignee: Otsuka Pharmaceutical Co., Ltd., Tokyo (JP)

( * ) Notice: Subject to any disclaimer, the term of this patent is extended or adjusted under 35 U.S.C. 154(b) by 0 days.

(21) Appl. No.: 09/601,478

(22) PCT Filed: Feb. 2, 1999

(86) PCT No.: PCT/JP99/00419

§ 371 (c)(1),
(2), (4) Date: Aug. 11, 2000

(87) PCT Pub. No.: WO99/40190

PCT Pub. Date: Aug. 12, 1999

(30) Foreign Application Priority Data

Feb. 3, 1998 (JP) ............................................ 10-038133
Mar. 5, 1998 (JP) ............................................ 10-073234
Apr. 28, 1998 (JP) ............................................ 10-134679

(51) Int. Cl.[7] .............................................. C07H 21/04
(52) U.S. Cl. ........................... 536/23.5; 530/350; 435/6; 435/91.2; 536/23.1; 536/24.3; 536/24.33
(58) Field of Search .............................. 536/23.1, 24.33, 536/24.3, 24.31, 23.5; 530/350; 435/6, 91.2

(56) References Cited

U.S. PATENT DOCUMENTS 5,356,817 A * 10/1994 Cole ........................... 436/64

FOREIGN PATENT DOCUMENTS

| WO | WO 97/21809 | 6/1997 |
| WO | WO/98/23747 | 6/1998 |
| WO | WO 98/23747 A2 * | 6/1998 |
| WO | WO 99/61612 | 12/1999 |

OTHER PUBLICATIONS

Lazar, E, et al, 1988, Transforming growth factor alpha: mutation of aspartic acid 47 and leucine 48 results in different biological activities, Mol. Cell. Biol., vol. 8, pp. 1247–1252.*
Burgess, Wh, et al, 1990, Possible dissociation of the heparin–binding and mitogenic activities of heparin–binding (acidic fibroblast) growth factor–1 from its receptor–binding activities, Journal of Cell Biology, vol. 111, pp. 2129–2138.*
Pohl, Al, et al, 1994, Neural network evaluation of multiple tumor markers for diagnosis of ovarian cancer using three different sets of patients (meeting abstract), Non–serial, 3rd Internatl. Conf. of the Mediterrenean Soc. of Tumor Marker Oncol.*
Genesis Group Associates, Inc., 1997, New tests may improve breast cancer prognosis, Genesis Report–Dx, vol. 6, No. 3 (summary only).*
Ward, Am, et al, 1985, Tumour markers, Developmental Oncology, vol. 21, pp. 91–106 (abstract only).*
Harris, PC, et al, 1995, Polycystic kidney disease 1: identification and analysis of the primary defect, Journal of the American Society of Nephrology, vol. 6, pp. 1125–1133.*
Ahn, Ah, et al, 1993, The Structural and functional diversity of dystrophin, Nature Genetics, vol. 3, pp. 283–291.*
Cawthon, Rm, et al, 1991, cDNA sequence and genomic structure of EV12B, a gene lying within a intron of the neurofibromatosis type 1 gene, Genomics, vol. 9, pp. 446–460.*
Tockman, Ms, et al, 1992, Considerations in bringing a cancer biomarker to clinical application, Cancer Research, supplement, vol. 52, pp. 2711s–2718s.*
USPTO Search Report US–09–601–478–2.oli.rge, Jan. 2001, search result No. 7, GenEmbl database, accession No. Z22264, Zabarovsky, et al.*
USPTO Search Report US–09–601–478–2.rng, Jan. 2001, search result No. 3, Geneseq database, accession No. V36270, WO98/23747–A2 (Schering Corp.).*
Kouichi Ozaki et al., Isolation and Characterization of a Novel Human Lung–specific Gene Homologous to Lysosomal Membrane Glycoproteins 1 and 2: Significantly Increased Expression in Cancers of Various Tissues, *Cancer Research*, Aug. 15, 1998, vol. 58, No. 16, pp 3499–3503.
Y. Shimada, et al., Cloning of a novel gene (INGIL) homologous to ING1, a candidate tumor suppressor, 1998 *Crytogenetics and Cell Genetics*, pp 232–235.

* cited by examiner

*Primary Examiner*—Donna C. Wortman
*Assistant Examiner*—Stephen L. Rawlings
(74) *Attorney, Agent, or Firm*—Sughrue Mion, PLLC

(57) ABSTRACT

This invention provides the TSC403 gene having a nucleotide sequence coding for the amino acid sequence of SEQ ID NO:1, which is a novel gene of great utility particularly in the field of research, diagnosis, therapy, etc. for cancer of the lung, among other diseases.

In addition, this invention provides the human ING1L gene comprising a nucleotide sequence coding for the amino acid sequence of SEQ ID NO:4, which is a novel human gene useful for regulating the cell cycle, inhibiting or activating cell proliferation, studies on metabolic aging or apoptosis of cells, pathological exploration, diagnosis and therapy of cancer and other diseases, and screening for the development of new drugs.

2 Claims, 10 Drawing Sheets

FIG. 1

Heart Brain Placenta Lung Liver Skeletal muscle Kidney Pancreas Spleen Thymus Prostate Testis Ovary Small intestine Colon P.B.L.

brain tumor
brain normal
kidney tumor
kidney normal
liver tumor
liver normal
lung tumor
lung normal breast tumor
normal breast
uterine tumor
normal uterine
fallopian tube tumor
normal fallopian tube
ovarian tumor
normal ovary

FIG. 4 esophagus tumor
normal esophagus
stomach tumor
normal stomach
colon tumor
normal colon
rectum tumor
normal rectum thyroid tumor
normal thyroid
adrenal tumor
normal adrenal
parotid tumor
normal parotid
lymphoma
normal lymph node

FIG. 5 kidney tumor
normal kidney
ureter tumor
normal ureter
bladder tumor
normal bladder
stomach tumor
normal stomach ovarian tumor normal tumor normal tumor normal tumor normal

FIG. 8

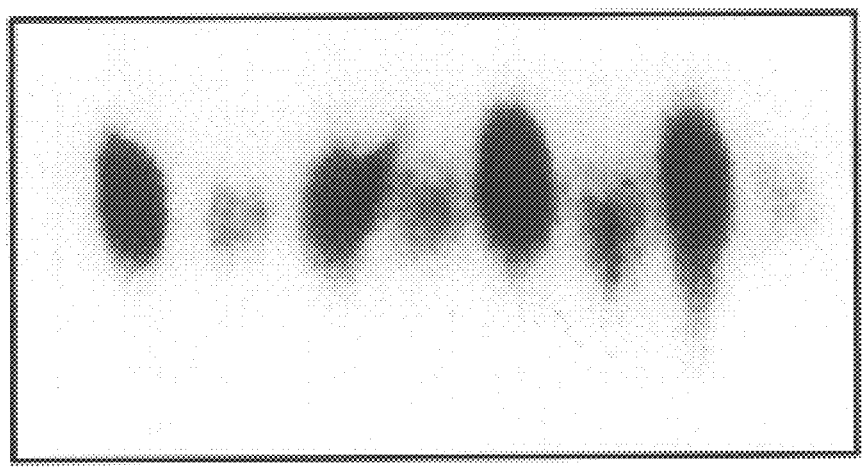

ISOLATED DNA MOLECULE ENCODING HUMAN TSC403

TECHNICAL FIELD

The invention relates to a gene of use as an index in the prophylaxis, diagnosis and therapy of human diseases and more particularly to a novel lung-specific human gene which is homologous to human 1 amp-1 and -2 [lysosomal membrane glycoprotein; Saito, O. et al., J. Biol. Chem., 267, 5700–5711 (1992); Sawada, R. et al., J. Biol. Chem., 268, 12675–12681 (1993); Sawada, R. et al., J. Biol. Chem., 269, 1425–1431 (1994)] and suspected to act as an oncogene.

The invention further relates to a novel human gene which is analogous to the rat, mouse, yeast, nematode, known human and other genes and, through the cDNA analysis, chromosome mapping and functional analysis of its cDNA, can be utilized in gene diagnosis and for the development of new therapeutic drugs.

In addition, the invention relates to novel proteins encoded by said genes and to specific antibodies thereto.

BACKGROUND ART

The genetic information in organisms is accumulated as arrays (DNA) of four kinds of bases, viz. A, C, G and T, in the cell nucleus, and this genetic information is conserved for maintenance of lineage and ontogenesis. In a human being, the number of such bases is said to be approximately three-billion ($3 \times 10^9$) and it is estimated that this population includes 50–100 thousand genes. The genetic information is involved in the maintenance of vital phenomena through the creation of regulatory proteins, structural proteins, enzymes, etc. along the flow of transcription of mRNA from genes (DNA) and ensuing translation into proteins.

It is generally acknowledged that any abnormality of the above flow from a gene to its translation product protein leads to an error of the life maintenance system inclusive of the proliferation and differentiation of cells, and can becauses of various diseases. The results of gene analyses made to this day suggest that the genes of various receptors, such as the insulin, LDL and other receptors, and those of metabolic enzymes associated with the growth and differentiation of cells, such as protease, ATPase, superoxide dismutase, etc., are considered to be useful tools for the development of pharmaceuticals.

However, the analysis of human genes and the study of their functions and relationships to various diseases are still in the inchoate stage and much remains to be known. Therefore, analysis of new genes, analytical explorations into the functions and relationships to diseases of such genes, and studies for the establishment of gene diagnostics exploiting the genes so analyzed, and pharmaceutical application studies on such genes are subjects of immense interest to this industry.

Meanwhile, carcinoma of the pancreas is one of the malignant tumors of the digestive system with the poorest prognosis, ranking fourth and fifth on the list of causes for cancer-related death in Japan and Western counties, respectively (Poston, J. G., et al., Gut., 32, 800–812 (1991)). The most important goal in cancer research is to identify changes in the genes in the early phase of oncogenesis. Identification of such changes should lead to the development of genetic tools for early diagnosis and novel therapeutic modalities for effective treatment of this lethal disease.

Elucidation of the physiological roles of such genes and the resulting information are important to the explication of the mechanisms of genesis and onset of neoplastic diseases, and have been demanded not only in the field of fundamental scientific research but also from the standpoint of characterization and treatment of malignant tumors in the pharmaceutical field.

DISCLOSURE OF INVENTION

Thus, assuming that a novel human gene be provided, its expression levels in various cells as well as its structure and functions could be elucidated and through analysis of expression products of the gene, the clarification of pathology, diagnosis and therapy of the diseases associated with the gene, such as hereditary diseases and cancers, would become feasible. The object of the invention is to provide such novel human genes.

With the above object in mind, the inventors did intensive research as described below. Thus, to begin with, the inventors synthesized cDNAs from the mRNAs extracted from various human tissues such as human fetal brain, adult blood vessel and placenta, cloned them into vectors to construct libraries, cultured *Escherichia coli* cells transformed with each library on agar medium picked up transformant colonies at random and transferred them to microtiter plates to prepare and register *E. coli* clones containing various human genes. Then, each of these clones was cultured, the DNA extracted and purified, and using the cDNA thus obtained as a template, an amplification reaction with chain termination specific to said 4 bases is carried out by the deoxy terminator method, and using an automatic DNA sequencer, the sequence of about 400 nucleotides from the 5' end of the human gene in each registered clone was determined. Based on the thus-obtained nucleotide sequence information on human genes, novel family genes similar to the known bacterial, yeast, nematoid, murine, human and other animal and plant genes were explored. The above technology for cDNA analysis is described in detail in the report of Fujiwara et al. [Fujiwara, Tsutomu, Saibo Kogaku (Cell Engineering), 14, 645–654 (1995)].

As a result, among the cDNA clones picked up arbitrarily from the human fetal brain cDNA library, the inventors found a clone harboring a novel gene which codes for an amino acid sequence having high homology to $p33^{ING1}$ which is considered to be a cancer-suppressive protein [GenBank A. C. No. AF001954, Garkavetsev, et al., Nature, Genet., 14, 415–420 (1996); Garkavetsev, et al., Mol. Cell. Biol., 17, 2014–2019 (1997); rewrote-GenBank A. C. No. AF0440767]. This invention has been developed on the basis of the above finding.

Furthermore, for the purpose of providing said information demanded by the industry, in particular a gene coding for a novel protein having homology to lamp-1 gene and lamp-2 gene, the inventors made an intensive exploration into the genes derived from various human tissues and succeeded in isolating and characterizing a novel lung-specific gene matching for the above purpose. This invention has been developed on the basis of the above finding.

Thus, in the first place, the invention provides a gene containing a nucleotide sequence coding for the amino acid sequence of SEQ ID NO:1 (hereinafter referred to TSC403 gene), in particular said gene which is a human gene.

In addition, the invention provides a novel protein encoded by said TSC403 gene (hereinafter referred to as TSC403 protein) and an antibody having a binding affinity for said protein.

Further, the invention provides a TSC403 gene which is any one of the following polynucleotides (a), (b) and (c), particularly said gene which is a human gene.

(a) a polynucleotide containing the nucleotide sequence of SEQ ID NO:2 or a complementary chain there; to (b) a polynucleotide which hybridizes to a DNA having the nucleotide sequence of SEQ ID NO:2 under stringent conditions; and (c) a polynucleotide having at least 95% homology to a polynucleotide coding for a polypeptide containing the amino acid sequence of SEQ ID NO:1

The invention further provides a TSC403 gene having the nucleotide sequence of SEQ ID NO:3.

The invention further provides an oligonucleotide having a sequence consisting of at least 15 consecutive nucleotides in the nucleotide sequence of SEQ ID NO:2 and a DNA fragment for use as a specific probe or primer for detecting genes having said oligonucleotide sequence.

Furthermore, in accordance with the invention, there is provided a human gene (hereinafter referred to as human ING1L gene) containing a nucleotide sequence coding for the amino acid sequence of SEQ ID NO:5.

This invention further provides a protein (hereinafter referred to as human ING1L protein) which is encoded by said human ING1L gene and an antibody binding said protein.

Further provided in accordance with this invention is a human ING1L gene comprising any one of the following polynucleotides (a), (b) and (c).

(a) a polynucleotide containing the nucleotide sequence of SEQ ID NO:6;

(b) a polynucleotide containing a nucleotide sequence which hybridizes to a DNA having the nucleotide sequence of SEQ ID NO:6 under stringent conditions; and (c) a polynucleotide having at least 95% homology to a polynucleotide coding for a polypeptide containing the amino acid sequence of SEQ ID NO:5.

Further provided in accordance with this invention is a human ING1L gene having the nucleotide sequence of SEQ ID NO:7.

In addition, according to the invention, there are provided an oligonucleotide having a sequence consisting of at least 15 consecutive nucleotides in the nucleotide sequence of SEQ ID NO:6 and a DNA fragment for use as a specific probe or primer for detecting genes having said oligonucleotide sequence.

Representation of amino acids, peptides, nucleotide sequences, nucleotides, etc. by abbreviations in this specification is in conformity with the rules recommended by IUPAC-IUB [IUPAC-IUB Communication on Biological Nomenclature, Eur. J. Biochem., 138, 9 (1984)], "Guideline for Preparation of a Specification or Equivalent Referring to a Nucleotide Sequence and/or an Amino Acid Sequence" (edited by the Patent Office of Japan) and the conventions relating to the use of codes or symbols in the art.

The TSC403 gene according to the invention is now described in detail.

As a specific example of the TSC403 gene according to the invention, there can be mentioned the gene deduced from the DNA sequence of a PCR product named "TSC403" as described in the Example which appears hereinafter. Its nucleotide sequence is presented in SEQ ID NO:3.

This gene is a human cDNA coding for a novel lung-specific protein having a sequence of 416 amino acid residues as shown in SEQ ID NO:1 (hereinafter referred to as "TSC403 protein") and this cDNA has a full length of 3198 nucleotides.

The TSC403 protein of the invention occurs as an expression product of the gene of the invention. A homology search using FASTA Program [Person, W. R., et al., Proc. Natl. Acad. Sci., USA, 85, 2444–2448 (1988)] against the GenBank/EMBL database revealed that this gene is homologous to human lamp-1 gene and lamp-2 gene (cf. the literature cited above).

In this connection, it is known that said human lamp genes are expressed at high levels in a highly metastatic colorectal cancer cell line and bind to E-selectin on the vascular endothelial cell. It is, therefore, suspected that these genes are associated with the malignancy of cancers (the literature cited above).

The TSC403 gene according to the invention is also a cancer-related gene, which is expected to find application as a cancer marker.

Furthermore, the chromosomal locus of this gene of the invention is 3q27 where chromosomal aberration is detected in various cancers. This fact, even alone, strongly suggests the relation this gene of the invention has to various neoplastic diseases.

Furthermore, the TSC403 gene according to the invention was found to show high expression in various cancer specimens, suggesting its value as a marker for predicting oncogenesis and malignancy.

Thus, the TSC403 gene or a gene product thereof in accordance with the invention provides the information or means of immense importance to the elucidation. understanding, diagnosis, prophylaxis and therapy of various neoplastic diseases such as colorectal cancer, cancer of the uterus, cancer of the ovary, cancer of the lung, and cancer of the pancreas, among others. Furthermore, this gene of the invention can be used with advantage in the development of new drugs which would induce expression of the gene for use in the treatment of said neoplastic diseases.

In addition, detection of expression of the gene of the invention or expression of its product in an individual or a given tissue as well as detection of amutation (deletion or point mutation) or expression abnormality of said gene can be exploited to advantage in the explication and diagnosis of said various neoplastic diseases.

The human ING1L gene of the invention is now described in detail.

As a specific example of the human ING1L gene according to the invention, there can be mentioned the gene deduced from the DNA sequence harbored by the clone named "GEN-146F11" and described in the Example which appears hereinafter. The nucleotide sequence of this gene is presented in the SEQUENCE LISTING. Thus, the gene harbored by this clone has a 840-nucleotide open reading frame (deduced amino acid translated region; the sequence is shown in SEQ ID NO:6) which codes for the sequence of 280 amino acid residues as shown in SEQ ID NO:5 in the SEQUENCE LISTING, and the full-length nucleotide sequence of the cDNA clone consists of 1078 nucleotides as shown in SEQ ID NO:7.

In the above sequence of SEQ ID NO:7, the initiation codon is located in the position 92-94 and the termination codon in the position 932-934. The polyadenylation signal-like sequence (ATTAAA) is located in the position 1058-1063.

As mentioned above, the human ING1L gene of the invention has high homology to $p33^{ING1}$ and can be utilized in the analysis of human genes based on its genetic information and studies on the relationships of various functions of the genes so analyzed to various diseases and further exploited in the gene diagnosis and gene therapy of the gene-related diseases and application studies on the genes in the pharmaceutical field. Thus, the functions of the protein (gene product) encoded by the human ING1L gene of the invention can be predicted from those of the known homologous genes, and as the result of provision of the gene of the invention, it is now possible to construct a recombinant protein by cloning the candidate gene in an expression vector and investigate its enzymatic activity, binding activity and other functions. Particularly, since the gene of the invention is suspected to function as an oncogene, this function can be utilized with advantage in the development of pharmaceuticals such as anticancer drugs.

The protein (hereinafter referred to as "human ING1L protein) encoded by the human ING1L gene of the invention has a Zn finger motif-like sequence in its C-terminal region and this region in particular is considered to have high homology to said $p33^{ING1}$.

In this connection, it has been reported that said $p33^{ING1}$ is inactivated in several cancer-derived cell lines including a mammary cancer cell line (the literature cited above). Moreover, it has recently been demonstrated that said $p33^{ING1}$ is negatively regulating cell proliferation through p53 which is known to be a cancer-suppressive gene product [Garkavetsev, etal., Nature, 391, 295–298 (1998)]. Furthermore, in various human neoplastic tissues, the expression level of human ING1L gene is specifically elevated. From these findings, it is suspected that the human ING1L protein is positively modulating cell proliferation through its interaction with p53.

Furthermore, in Northern blot analysis, expression of the human ING1L gene of the invention was found in all the 16 human adult organ-derived tissues tested and enhancement of its expression was noted in several neoplastic tissues including colorectal cancer, cancer of the esophagus, cancer of the uterine tube, and stomach cancer as compared with the normal tissues. These findings suggest that the gene of the invention can be used for the diagnosis of neoplastic and other diseases associated with it by checking for the expression thereof in various tissues and, as a corollary, finds application in the screening for antimitotic compounds or anticancer compounds.

The gene of the invention specifically includes polynucleotides containing the nucleotide sequences of SEQ ID NOS:2 and 6 which code for the amino acid sequences of SEQ ID NOS:1 and 5, respectively, polynucleotides which hybridize to DNAs containing the nucleotide sequences of SEQ ID NOS:2 and 6 under stringent conditions, and polynucleotides having at least 95% homology to polynucleotide encoding the amino acid sequences of SEQ ID NOS: 1 and 5.

Therefore, the gene of the invention includes those genes which encode amino acid sequences corresponding to certain modifications of the above-defined amino acid sequences and those genes which have a defined degree of homology to the above-defined nucleotide sequences.

Thus, the gene of the invention includes, among others, genes containing nucleotide sequences coding for the amino acid sequences resulting from the deletion, substitution or addition of one or a plurality of amino acids from, in or to the amino acid sequence of SEQ ID NO:1 or 5 (i.e. modified amino acid sequences). The gene having a nucleotide sequence coding for such a modified amino acid sequence need only be such that by utilizing it, the gene of the invention coding for the unmodified amino acid sequence can be detected.

Incidentally, while such modifications (mutation etc.) of amino acid sequences may be spontaneous, e.g. mutations and post-translational modifications, the modifications can be made artificially as well by utilizing a gene of the natural origin (for example, a specific gene of the invention).

The means for making such artificial modifications includes genetic engineering techniques such as site-specific (-directed) mutagenesis [Methods in Enzymology, 154:350, 367–382(1987); ditto 100:468(1983); Nucleic Acids Res., 12: 9441 (1984); Zoku Seikagaku Jikken Koza 1 "Idenshi Kenkyuho II" [Experimental Biochemistry Series 1 "Methods for Gene Research II" (edited by Japanese Biochemical Society), p105 (1986) ], etc. and chemical synthetic techniques such as the phosphotriester method and the phosphoamidate method [J. Am. Chem. Soc., 89: 4801 (1967); ditto 91: 3350 (1968); Science, 150: 178 (1968); Tetrahedron Lett., 22: 1859 (1981); ditto 24: 245 (1983)] as well as a suitable combination of such techniques.

As one example of the gene according to the invention, the gene comprising a polynucleotide having the nucleotide sequence of SEQ ID NO:2 or 6 or a complementary sequence thereto can be mentioned. This nucleotide sequence represents an example of combination of codons for each amino acid residue of the above amino acid sequence (SEQ ID NO:1 or 5). Of course, the gene of the invention is not limited to the above combination but the gene having a nucleotide sequence designed by. selecting an arbitrary combination of codons for each of said amino acid residues can be employed. Selection of said codons can be made in the routine manner. In this selection, the codon frequency of the host to be used may be taken into consideration [Nucleic Acids Res., 9: 43 (1981)].

Furthermore, while the gene of the invention is shown as the nucleotide sequence of a single-stranded DNA as, for example, shown in SEQ ID NO:3 or 7 the invention of course encompasses a polynucleotide comprising a nucleotide sequence complementary to such a nucleotide sequence and a component containing both of them as well and, moreover, is not limited to a DNA such as cDNA.

Furthermore, as mentioned above, the gene of the invention is not limited to one comprising a polynucleotide having the nucleotide sequence of SEQ ID NO:2 or 6 or a complementary sequence thereto but includes one comprising a nucleotide sequence having a given degree of homology to such a nucleotide sequence. More particularly, there is included the gene comprising a polynucleotide having at least 95% homology to a polynucleotide coding for a polypeptide having the amino acid sequence of SEQ ID NO:1 or 5.

Moreover, the gene of said nucleotide sequence having a defined homology includes one that hybridizes to a DNA having the nucleotide sequence of SEQ ID NO:2 or 6 under stringent conditions such as those described below and does not lose the DNA even when the hybrid is washed under given conditions.

As an example, there can be mentioned a gene having a nucleotide sequence which, when hybridized to a DNA having the nucleotide sequence of SEQ ID NO:2 or 6 in 6×SSC at 65° C. overnight or in 4×SSC supplemented with 50% formaldehyde at 37° C. overnight and, then, washed in 2×SSC at 65° C. for 30 minutes, will not be disengaged from the DNA. Here, SSC stands for standard saline-citrate buffer (standard saline citrate; 1×SSC=0.15 M NaCl, 0.015 M sodium citrate). A preferred example of said gene is a gene having a nucleotide sequence which, even when hybridized to a DNA having the nucleotide sequence of SEQ ID NO:2 or 6 in 7% polyethylene glycol (PEG)/10% sodium dodecyl sulfate (SDS) at 65° C. overnight and washed in 0.1×SSC/0.1% SDS at 65° C. for 30 minutes, will not be disengaged from the DNA.

The gene of the invention can be easily produced and acquired by the standard genetic engineering techniques

[Molecular Cloning 2d Ed, Cold Spring Harbor Lab. Press (1989); Zoku Seikagaku Jikaen Koza "Idenshi Kenkyuho I, II, III" [New Experimental Biochemistry Series "Methods for Gene Research I, II, III" (edited by Japanese Biochemical Society), (1986), etc. ] based on the sequence information on the specific examples shown in SEQ ID NO:3 or 7.

More particularly, the objective gene can be acquired by constructing a cDNA library from a suitable source containing the gene of the invention and selecting the desired clone from this cDNA library using a suitable probe or antibody specific to the gene of the invention in the per se known manner [Proc. Natl. Acad. Sci., USA., 78: 6613 (1981); Science, 222: 778 (1983), etc.].

In the above procedure, the cDNA source includes to various cells or tissues in which the gene of the invention is expressed and cultured cells derived therefrom. Particularly in the case of the TSC403 gene of the invention, lung tissues can be mentioned by way of example. Isolation of the whole RNA from such a source, isolation and purification of mRNA, synthesis of cDNA, and cloning thereof can all be carried out in the routine manner. cDNA libraries are also commercially available. In the practice of the invention, such commercial cDNA libraries, for example those available from Clontech Lab. Inc., can also be employed.

The method of screening for the gene of the invention from a cDNA library is not particularly restricted, either, but a conventional method can be selectively employed. To be specific, selection of a cDNA clone by an immunoscreening technique using a specific antibody against the protein produced by the cDNA, the plaque hybridization or colony hybridization technique using a probe having a selective binding affinity for the objective DNA sequence, or a combination thereof can be mentioned by way of example.

As to the probe to be used in the above procedure, it is generally useful to use a DNA chemically synthesized according to the nucleotide sequence information on the gene of the invention. Of course, it is also possible to use the gene already obtained or a fragment thereof as said probe.

The nucleotide sequence which can be used as said probe includes a partial nucleotide sequence corresponding to SEQ ID NO:2 or 6 but consisting of at least 15 consecutive nucleotides, preferably within the range of 20–30 nucleotides. Moreover, positive clones containing the above respective sequences can also be utilized as said probe.

Said screening can be carried out by the procedure which uses, as the screening probe, a set of sense and antisense primers based on the partial amino acid sequence information about a natural extract isolated and purified from a given cell line or tissue.

Furthermore, said screening can also be carried out by the protein interaction cloning procedure using the TSC403protein or human ING1L protein in lieu of said specific antibody.

In the invention, the expression of mRNA in cells under different conditions or between a plurality of cell groups can be studied by direct comparison using the differential display method [Liang, P., et al., Science, 257, 967–971 (1992)].

In obtaining the gene of the invention, DNA/RNA amplification by PCR [Science, 230, 1350 (1985)] can also be used with advantage. Particularly in case where a full-length cDNA can hardly be obtained from a library, the RACE [rapid amplification of cDNA ends] method [Jikken Igaku (Experimental Medicine), 12(6): 35 (1994)], in particular the 5'-RACE method [Frohman, M. A., et al., Proc. Natl. Acad. Sci., USA., 8: 8998 (1988)], can be used with advantage. The primers for use in such PCR methods can be judiciously established according to the sequence information on the gene of the invention and can be synthesized by the conventional procedure.

Isolation and purification of the amplified DNA/RNA fragment can be carried out by the conventional techniques as mentioned hereinbefore, for example by gel electrophoresis.

The nucleotide sequence of the gene of the invention or any of various DNA fragments thereof can be determined in the routine manner, for example by the dideoxy method [Proc. Natl. Acad. Sci., USA., 74: 5463 (1977)], the Maxam-Gilbert method [Methods in Enzymology, 65: 499 (1980)] or, more expediently, by means of a commercial sequencing kit.

With the gene of the invention, the gene product can be produced easily, on a high production scale, and with good reproducibility by the standard genetic engineering technology.

The invention further provides a vector (expression vector) harboring said TSC403 gene or human ING1L gene, host cells transformed by using said vector, and a method of producing TSC403 protein or human ING1L protein which comprises growing said host cells.

Production of said TSC403 protein and human ING1L protein can be carried out by the standard recombinant DNA technology [Science, 224: 1431 (1984): Biochem. Biophys. Res. Comm., 130: 692 (1985): Proc. Natl. Acad. Sci., USA., 80: 5990 (1983), and the reference literature cited hereinabove].

As said host cells, whichever of prokaryotic cells and eucaryotic cells can be employed. As the prokaryotic host, various procaryotes which are commonly employed, such as *Escherichia coli* and *Bacillus subtilis*, can be liberally employed. The preferred host cells are those derived from *Escherichia coli*, particularly cells of *E. coli* K12.

The eucaryotic host cells include cells of vertebrate and yeasts, among others. Among the former cells, the monkey cell line COS [Cell, 23: 175 (1981)], Chinese hamster ovarian cells and the dihydrofolate reductase-defective line thereof [Proc. Natl. Acad. Sci., USA., 77: 4216 (1980)] can be mentioned as examples. As to the latter cells, cells of yeasts belonging to the genus Saccharomyces can be mentioned as examples but these are not exclusive choices.

When prokaryotic cells are used as host cells, a vector which can be replicated in the host cell is selected and, for expression of the gene, an expression plasmid provided with a promoter and the SD (Shine-Dalgarno) sequence upstream of the gene of the invention, as well as an initiation codon (e.g. ATG) necessary to start protein synthesis, can be employed with advantage. As the vector mentioned above, it is usual to employ an *E. coli*-derived plasmid, such as pBR322, pBR325, pUC12, pUC13, etc., although these are not exclusive choices and various known other vectors may be utilized. As commercial vectors for expression systems using *E. coli*, pGEX-4T (Amersham Pharmacia Biotech), pMAL-c2, pMAL-p2 (New England Biolabs), pET21, pET21/lacq (Invitrogen), pBAD/His (Invitrogen), among others, can be mentioned by way of example.

As the expression vector to be used when cells of a vertebral animal are employed, usually a vector having a promoter region upstream of the gene to be expressed, RNA splice sites, polyadenylation site, transcription end sequence, etc. can be mentioned, and where necessary, the vector further has a replication origin. As a specific example of the above vector, pSV2dhfr containing an early promoter of SV40 [Mol. Cell. Biol., 1: 854 (1981)], for instance, can be mentioned. Aside from the above, various other known commercial vectors can be used. As commercial vectors which can be used in expression systems utilizing animal cells, there can be mentioned various vectors available for animal cell use, such as PEGFP-N, pEGFP-C (Clontech), pIND (Invitrogen), pcDNA3.1/His (Invitrogen), etc. and vectors available for insect cell use, such as pFastBacHT (Gibco BRL), pAcGHLT (PharMingen), pAc5/V5-His, pMT/V5-His and pMT/Bip/V5-His (all Invitrogen).

As a specific example of the expression vector which can be used when yeast cells are used as the host cells, pAM82 having a promoter for the acid phosphatase gene [Proc. Natl. Acad. Sci., USA., 80: 1 (1983)] can be mentioned. The commercial expresion vectors for yeast cell use include to pPICZ (Invitrogen) and pPICZ (Invitrogen).

The promoter is not particularly restricted, either. When a bacterial strain of the genus Escherichia is used as the host, tryptophan (trp) promoter, lpp promoter, lac promoter, recA promoter, PL/PR promoter, etc. can be used with advantage. When the host is an organism of the genus Bacillus, SP01 promoter, SP02 promoter, penP promoter, etc. are preferred choices. The promoter which can be used with advantage when a yeast is used as the host includes pH05 promoter, PGK promoter, GAP promoter and ADH promoter, among others. The preferred promoter in cases where animal cells are used as said host cells includes SV40-derived promoter, retrovirus promoter, metallothionein promoter, heat shock promoter, cytomegalovirus promoter and SR promoter, among others.

As expression vectors for the gene of the invention, the conventional fusion protein expression vector can also be used with advantage. As an example of the vector of this type, pGEX (Promega) for expression of a fusion protein with glutathione-S-transferase (GST) can be mentioned.

The method of introducing said objective recombinant DNA (expression vector) into the host cell (transformation method) is not particularly restricted, either, but various standardized methods can be utilized. Culture of the resultant transformant can also be performed in the routine manner. By such culture, the objective protein encoded by the gene of the invention is expressed, produced, and accumulated in the transformant cell or secreted extracellularly or on the cell membrane.

The medium for said culture can be judiciously selected from among the conventional media according to the type of host cells adopted, and culture can also be carried out under conditions suited for proliferation of the host cells.

The recombinant protein thus produced can be optionally isolated and purified by various isolation procedures utilizing its physical, chemical or other properties [Seikagaku (Biochemical) Data Book II, pp.1175–1259, 1st Ed., 1st Impression, Jun. 23, 1980, Tokyo Kagaku Dojin; Biochemistry, 25(25): 8274 (1986); Eur. J. Biochem., 163:313(1987); etc.]. The procedures mentioned above specifically include the standard reconstitution treatment, treatment with a protein precipitating agent (salting out), centrifugation, osmotic shock method, sonic disruption, ultrafiltration, various kinds of chromatography, e.g. molecular sieves chromatography (gel filtration), adsorption chromatography, ion exchange chromatography, affinity chromatography, high performance liquid chromatography (HPLC), etc., dialysis, and their combinations. The particularly preferred procedure is affinity chromatography using a column conjugated with a specific antibody against the TSC403 protein or human ING1L protein according to the invention.

The invention further provides the novel TSC403 protein or human ING1L protein obtainable as above and the technology of producing those proteins. The protein according to the invention finds application in the pharmaceutical field as mentioned hereinbefore.

Moreover, the protein of the invention can be used as an immunogen for construction of a specific antibody against said protein. The component for use here as the antigen may be the protein produced in a large amount by any of said genetic engineering techniques or a fragment thereof, and by using such an antigen, the objective antiserum (polyclonal antibody) and monoclonal antibody can be obtained.

The production technology for such antibodies is well known to those skilled in the art and the production of antibodies relevant to the invention can also be made in accordance with such established technology (Zoku Seikagaku Koza "Men-eki Seikagaku Kenkyuho" (New Immunobiochemistry Series, "Methods in Immunobiochemistry"), edited by Japanese Biochemical Society (1986), among others].

For example, the immune animal for use in harvesting the antiserum can be liberally selected from among ordinary animals such as the rabbit, guinea pig, rat, mouse, chicken, goat and sheep, and immunization with said antigen and collection of blood can also be carried out in the routine manner.

Preparation of said monoclonal antibody can also be carried out in the routine manner, i.e. by constructing a fusion cell from the plasma cell (immune cell) of an animal immunized with said immunogen and a plasmocytoma cell, selecting a clone producing the objective antibody, and growing the clone. The immune animal is generally selected in consideration of its compatibility with the plasmocytoma cell to be used for cell fusion and usually the mouse or the rat is used with advantage. Immunization can be carried out in the same manner as in the preparation of said antiserum, and optionally the usual adjuvant can be used in combination with the antigen.

The plasmocytoma cell to be used for said fusion is not particularly restricted but may be any of various myeloma cells such as p3 (p3/x63-Ag8) [Nature, 256:495–497 (1975)], p3-U1 [Current Topics in Microbiology and Immunology, 81: 1–7 (1978)], NS-1 [Eur. J. Immunol., 6: 511–519 (1976)], MPC-11 [Cell, 8: 405–415 (1976)], SP2/0 [Nature, 276: 269–271 (1978)], etc., R210 [Nature, 277: 131–133 (1979)], etc. from rats and cells derived therefrom.

The fusion between said immune cell and plasmocytoma cell can be effected in the presence of a conventional fusion promoter, such as polyethylene glycol (PEG), Sendai virus (HVJ) or the like, in accordance with a known protocol. Isolation of the objective hybridoma can also be carried out by the known procedure [Meth. in Enzymol., 73: 3 (1981); said Zoku Experimental Biochemistry Series; etc. ].

The search for the objective antibody-producing cell line and the preparation of a monoclonal antibody can also be carried out in the conventional manner. For example, the search for an antibody producing line can be made by various techniques which are generally used for detection of antibodies, such as ELISA [Meth. in Enzymol., 70: 419–439 (1980)], plaque method, spot method, agglutination reaction method, Ouchterlony method, radioimmunoassay, etc., using the protein of the invention as an antigen.

Isolation of the antibody of the invention from the hybridoma obtained as above can be carried out by the method which comprises growing the hybridoma in the routine manner and recovering the antibody as a culture supernatant or the method which comprises administering the hybridoma to a compatible mammal to let it multiply in vivo and recovering the antibody in the form of an ascite fluid. The former method is suitable for the preparation of a high-purity antibody, while the latter method is suited for high production. The antibody produced in this manner can be purified by the routine procedure such as salting out, gel filtration, affinity chromatography or the like.

The antibody thus obtained is characterized in that it is capable of binding the protein of the invention. This characteristic can be exploited for the purification of the protein of the invention and the assay and identification of the protein by an immunological technique. The invention further provides such a novel antibody.

Based on the sequence information on the gene of the invention, which has been generated by the invention, the expression of the gene of the invention in the individual or in various tissues can be detected by utilizing a part or the whole of the nucleotide sequence of said gene.

In the invention, for the purpose of detecting the presence of a TSC403 gene or human ING1L gene whose expression level is elevated in a cancer tissue, one may prepare a biological sample, such as a blood or serum sample, optionally extract the DNA, and carry out an analysis to see whether the sample contains a susceptible TSC403 gene or human ING1L gene.

In accordance with the invention, for the purpose of detecting the presence of a marker of malignancy in cells or tissues, progression of malignancy to a prodromal disturbance, or prognosis, a biological sample of malignancy is prepared and analyzed for the presence of a TSC403 or human ING1L oncogene. By utilizing this technique, the presence of such a marker of malignancy in cells or a tissue, progression of malignancy to a prodromal disturbance, or prognosis can be detected. Therefore, the invention enables the diagnosis of a cancer, evaluation of the effect of a cancer therapy or prediction of the prognosis of a cancer.

The above detection can be carried out as follows. For example, based on the information on TSC403 gene or human ING1L gene as obtained by using a sample from a tumor-bearing patient, a DNA fragment designed for use in the screening for TSC403 gene or human ING1L gene and/or the amplification of the gene is first prepared. The DNA fragment mentioned above includes the following.

(1) The fragment having the nature of a probe for plaque hybridization, colony hybridization, Southern blotting, Northern blotting, etc.

(2) The fragment having the nature of a probe for preparation of the entire or partial DNA fragment of TSC403 gene or human ING1L gene as amplified by PCR, that is a polymerase chain reaction for amplifying a nucleotide sequence with a polymerase.

For the construction of such DNA fragments, a primer having the same sequence as TSC403 gene or human ING1L gene is first prepared. Using this primer as a screening probe, it is reacted with a biological sample (nucleic acid sample) to confirm the presence of a gene having the TSC403 gene sequence or human ING1L gene sequence.

The above nucleic acid sample can be prepared by various methods providing for easy detection of the target sequence, such as denaturation, restricted digestion, electrophoresis or dot blotting.

The method of said screening is preferably PCR from the standpoint of sensitivity. This method is not particularly restricted inasmuch as it employs a TSC403 gene fragment or a human ING1L gene fragment as the primer and it may be any of the known protocols [Science, 230: 1350–1354 (1985)] and all PCR versions that are newly developed or expected to be used in the future [Sakaki, Y. et al. (ed.), Jikken Egaku (Experimental Medicine), Supplement 8(9) (1990), Yodosha; Protein·Nucleic Acid ·Enzyme; Special Supplement, Kyoritsu Publishing Co., 35(17) (1990)].

The DNA fragments for use as primers are chemically synthesized oligo-DNAs. Those oligo-DNAs can be synthesized by using an automatic DNA synthesizer, e.g. Pharmacia LKB Gene Assembler Plus (Pharmacia). The length of the primer (sense primer or antisense primer) may for example be the equivalent of about 10–50 nucleotides, more preferably about 15–30 nucleotides.

The probe for use in the above screening is usually a labeled probe but may be an unlabeled probe. The screening may depend on specific binding with a directly or indirectly labeled ligand. The method of labeling a probe or a ligand is known in the art and the relevant prior art includes nick translation, random priming, and kinase treatment, among others. The substance which can be used as the label includes radioisotopes, biotin, fluorescent groups, chemiluminescent groups, enzymes and antibodies which can be taken up by way of such known methods.

The above-mentioned detection can be performed in the routine manner. For example, RNA amplification by RT-PCR [reverse transcribed-polymerase chain reaction; E. S. Kawasaki, et al., Amplification of RNA. In PCR Protocol, A Guide to Methods and Applications, Academic Press, Inc., SanDiego, 21–27 (1991)], Northern blot analysis [Molecular Cloning, Cold Spring Harbor Lab. (1989)], determination on the cellular level, e.g. in situ RT-PCR [Nucl. Acids Res., 21:3159–3166(1993)] and in situ hybridization, NASBA method [nucleic acid sequence-based amplification, Nature, 350: 91–92 (1991)], modifications of these techniques which are known in the art, and various other methods can invariably be used with success.

The method for assay according to the invention can be carried out expediently by utilizing an assay reagent kit for detection of TSC403 gene or human ING1L gene in samples. The invention further provides an assay kit for detection of TSC403 gene or human ING1L gene which contains said TSC403 gene fragment or human ING1L gene fragment.

It is important that this assay kit contain at least a DNA fragment hybridizing to a part or the whole of the nucleotide sequence of SEQ ID NO:2 or 6 or a complementary nucleotide sequence thereto as an essential component. As the other components, the kit may contain a labeling agent and reagents necessary for PCR, such as Taq DNA polymerase, deoxynucleotide triphosphate, and primers, among others.

The labeling agent includes radioisotopes and chemical modifiers such as fluorescent substances. These may be used as pre-conjugated to the DNA fragment.

For convenience in practice of the assay, the assay kit of the invention may contain a suitable reaction diluent, a standard antibody, a buffer, a washing buffer, a reaction stopper solution and so forth.

The invention further provides a method for cancer diagnosis utilizing the above assay method, a diagnostic reagent for use in said diagnosis, and a diagnostic kit.

By sequencing the TSC403 gene or human ING1L gene in a test sample as obtained by using the above assay method of the invention, either directly or indirectly by the conventional procedure, it is possible to discover a novel TSC403 or human ING1L-related gene (mutant gene) which is highly homologous to the wild type TSC403 gene or wild type human ING1L gene. Therefore, the invention further provides a method of screening for a TSC403-related gene or human ING1L-related gene in a test sample which comprises performing said assay and sequencing the TSC403 gene or human ING1L gene in the sample.

Moreover, by utilizing the protein encoded by the TSC403 gene or human ING1L gene of SEQ ID NO:1 or 5, a protein having an amino acid sequence resulting from the deletion, substitution or addition of one or a plurality of amino acids from, in or to said sequence of SEQ ID NO:1 or 5, or an antibody against such a fragment (polyclonal antibody or monoclonal antibody; hereinafter referred to as "TSC403 antibody" or "human ING1L antibody"), said wild type TSC403 gene, wild type human ING1L gene, mutant TSC403 gene and mutant human ING1L gene can be successfully assayed.

The invention further provides a method for assay of such a wild type TSC403 gene, a wild type human ING1L gene, a mutant TSC403 gene or a mutant human ING1L gene.

According to this assay methodology, the severity of disturbance in a neoplastic state or the malignancy of a neoplasm can be detected from a change in the wild type TSC403 gene or wild type human ING1L gene. The change mentioned above can be determined or detected by the sequencing of the TSC403 gene or human ING1L gene by any of the above-mentioned conventional sequencing techniques, and more preferably by the assay method using said TSC403 antibody or human ING1L antibody. In this manner, the presence of an anomaly (mutation) in the TSC403 protein or human ING1L protein in a test sample or the presence or absence of the TSC403 protein or human ING1L protein can be detected.

In the assay procedure of the invention which utilizes an anti-TSC403 antibody or anti-human ING1L antibody, the antibody can be used to immunoprecipitate the TSC403 protein or human ING1L protein from a solution containing a biological material obtained from a human subject, such as blood or serum, or caused to react with TSC403 protein or human ING1L protein on the polyacrylamide gel Western blot or on the immunoblot.

Furthermore, by utilizing the anti-TSC403 antibody or anti-human ING1L antibody in an immunohistochemical assay procedure, the TSC403 protein or human ING1L protein in a paraffin section or a frozen tissue specimen can be detected. The production technology and purification procedure which can be used for said anti-TSC403 antibody or anti-human ING1L antibody are well known in the art. Such known techniques can be utilized for the production and purification of said antibody.

The more preferred protocol relevant to the detection of a wild type TSC403 or human ING1L, or a mutant thereof, includes a sandwich assay using amonoclonal antibody and/or a polyclonal antibody. Among other preferred detection techniques are enzyme-linked immunosorbent assay (ELISA), radioimmunoassay (RIA), immunoradiometric assay (IRMA) and immunoenzymometric assay (IEMA).

The invention further provides a TSC403 protein receptor or human ING1L protein receptor existing in a cell membrane fraction or a cell surface and having binding activity for TSC403 protein or human ING1L protein. This TSC403 protein receptor or human ING1L protein receptor can be produced and obtained, for example by adding a labeled TSC403 protein or human ING1L protein to a cell membrane fraction containing the receptor or a biological sample containing the same, extracting, isolating and purifying the resulting receptor-protein conjugate (TSC403 protein-binding reaction product or human ING1L protein-binding reaction product) and identifying the amino acid sequence of the isolated product. The preparation and sequencing of the TSC403 protein or human ING1L protein receptor can be easily made by those skilled in the art according to the established procedures The TSC403 protein receptor or human ING1L protein receptor according to the invention, or fragments thereof, can be applied to the screening for various drugs. By such technology, compounds capable of reacting with said receptor (low molecular compounds, high molecular compounds, proteins, protein fragments, antigens, antibodies, etc.) can be screened out. The receptor, or a fragment thereof, which is to be used in such screening can be put to use as immobilized on a suitable solid matrix or in the form of a free substance in a solution transported to the cell surface.

An example of the above pharmacoscreening is the screening in which procaryotic or eucaryotic host cells transformed stably with a recombinant protein expressing the TSC403 protein or human ING1L protein, or a fragment thereof, are used in, preferably, a competitive binding assay. As an alternative, said host cells, whether in the free form or as immobilized, are used in the standard binding assay. More particularly, the above pharmacoscreening may comprise reacting the TSC403 protein receptor or human ING1L protein receptor, or a fragment thereof, with the TSC403 protein or human ING1L protein, or a fragment thereof, in the presence of a candidate drug, to cause formation of a complex and detecting the degree of inhibition of the complex formation by the above candidate drug.

Thus, in accordance with the invention, there can be provided a method for pharmacoscreening which comprises contacting a candidate drug with the TSC403 protein receptor or human ING1L protein receptor, or a fragment thereof and, then, detecting the presence of the resulting complex or the presence of a complex of the TSC403 protein receptor or human ING1L protein receptor, or a fragment thereof, and the ligand by a per se known technique.

Furthermore, by assaying TSC403 protein receptor activity or human ING1L protein receptor activity, it is possible to evaluate whether a candidate drug is capable of antagonizing the TSC403 protein receptor or human ING1L protein receptor and accordingly inhibiting TSC403 protein activity or human ING1L protein activity, for example mitosis-promoting activity.

In such a competitive binding assay, the TSC403 protein receptor or human ING1L protein receptor, or a fragment thereof, is labeled. When the free TSC403 protein receptor, human ING1L protein receptor or fragment thereof is separated from the corresponding complex and the labeling amount of the free (non-complex-forming) substance is measured, the measured value serves as a yardstick of the binding of the candidate drug to the TSC403 protein receptor or human ING1L protein receptor. Furthermore, said measured value serves also as a measure of inhibition of the binding of the TSC403 protein receptor or human ING1L protein receptor to the TSC403protein or human ING1L protein. By analyzing a small peptide (pseudopeptide) of TSC403 protein or human ING1L protein in this manner, the candidate drug can be assayed as a substance having TSC403 protein receptor antagonizing activity or human ING1L protein receptor antagonizing activity.

Another protocol for pharmacoscreening in accordance with the invention is that of screening for a compound having an adequate binding affinity for the TSC403 protein receptor or human ING1L protein receptor. Briefly, this procedure comprises synthesizing a large number of different test peptide compounds on a solid support such as the surface of a plastic pin or other material, reacting the test compounds with the TSC403 protein receptor or human ING1L protein receptor and, after washing, detecting the binding reaction products by a known method [e.g. PCT patent publication No. WO 84-03564].

The purified TSC403 protein receptor or human ING1L protein receptor can be directly coated on the plate to be used in said pharmacoscreening procedure. Moreover, the antibody may be captured with a non-neutralizing antibody against the polypeptide and the TSC403 protein receptor or human ING1L protein receptor be immobilized on a solid phase.

The invention is further directed to the use of a competitive pharmacoscreening assay. For the binding to the TSC403 protein receptor or human ING1L protein receptor, or a fragment thereof, a neutralizing antibody capable of specific binding to the TSC403 protein receptor or human ING1L protein receptor is caused to compete with the candidate compound. By such a competitive reaction with the neutralizing antibody, the presence of any peptide having one or more antigenic determinants of the TSC403 protein receptor or human ING1L protein receptor can be detected.

Furthermore, in connection with pharmacoscreening, a still another method comprises the use of a host eucaryotic cell line or cells containing a nonfunctional TSC403 gene or nonfunctional human ING1L gene. The host cell line or cells are caused to multiply in the presence of a candidate drug for a predetermined time and the velocity of growth of the host cells is determined to see whether, for example, the candidate drug is capable of inhibiting growth of the cells. The means for measuring said velocity of growth includes a method of determining the biological activity of the TSC403 protein receptor or human ING1L protein receptor.

Furthermore, in accordance with the invention, for the development of a more active or stable derivative of TSC403 protein or human ING1L protein or of a drug which will enhance or interfere with the function of TSC403 protein or human ING1L protein in vivo, it is possible to construct bioactive proteins, or their structural analogs, with which said protein would interact, such as a TSC403 protein or human ING1L protein receptor agonist, a TSC403 protein or human ING1L protein receptor antagonist, or a TSC403 protein or human ING1L protein inhibitor, for instance. The structural analogs mentioned above can be characterized by analysis of the three-dimensional structure of a complex between TSC403 protein or human ING1L protein and a third-party protein by X-ray crystallography or computer modeling or a combination of such techniques. The structural information on such structural analogs can also be obtained by protein modeling based on the structures of homologous proteins.

As a method for providing said more active or stable TSC403 protein derivative or human ING1L protein derivative, there can be mentioned an alanine scan technique. This technique comprises substituting an alanine residue for each of certain amino acid residues of said protein and determining the effect of substitution on the activity of the resulting protein. In other words, this technique is such that by said substitution for amino acid residues of the protein and analysis, the domain of significance to the activity or stability of the protein is determined. This technique enables design of a more active or stable TSC403 protein derivative or human ING1L protein derivative.

Furthermore, it is now possible to isolate a target-specific antibody selected by a functional assay and analyze its crystal structure. As a rule, the pharmacore providing a basis for subsequent drug design can be obtained by this approach. Through the generation of an anti-idiotype antibody for a functional pharmacoactive antibody, a peptide can be identified or isolated from a chemically or biologically constructed peptide bank. Hence, the selected peptide is also expected to serve as a pharmacore.

Thus, it is now possible to design and develop drugs having TSC403 protein or human ING1L protein inhibitor, agonist or antagonist activity for TSC403 protein or human ING1L protein having improved activity, stability and other characteristics.

It is also possible to prepare a sufficient amount of TSC403 protein or human ING1L protein by using a cloned TSC403 gene or cloned human ING1L gene and carry out X-ray crystallographic and other analytical investigations. Furthermore, as the result of provision of the TSC403 protein or human ING1L protein of SEQ ID NO:1 or 5 according to the invention, it is now possible to provide a computer modeling program or technique as a substitute for X-ray crystallography or as an adjunct thereto.

The invention enables construction of a TSC403 gene-bearing knockout mouse (mutant mouse) or human ING1L gene-bearing knockout mouse (mutant mouse). By this approach, it can be ascertained which region of the nucleotide sequence of the TSC403 gene or human ING1L gene influences said divergent activities of TSC403 protein or human ING1L protein in vivo, that is to say what functions TSC403 gene products, human ING1L gene products, modified-TSC403 gene products or modified-human ING1L gene products would have in vivo.

This is a technique for modifying the genetic information of an organism intentionally by utilizing a homologous recombination of genes, and a protocol using mouse embryonic stem cells (ES cells) is known [Capecchi. M. R., Science, 244, 1288–1292 (1989)].

The above construction of mutant mice belongs to the expertise of those killed in the art and the wild type TSC403 gene, wild type human ING1L gene, mutant TSC403 gene or mutant human ING1L gene according to the invention can be subjected to this modification [Tetsuo Noda (ed.): Jikken Igaku (Experimental Medicine), Supplement, 14(20) (1996), Yodosha] to thereby construct said respective mutant mice in an expedient manner. By utilizing this technique, it is possible to design and develop drugs having TSC403 protein or human ING1L protein inhibitor, agonist or antagonist activity for the protein having improved TSC403 protein activity or stability or improved human ING1L protein activity or stability.

Thus, the invention further provides a specific primer for detection of the TSC403 gene or human ING1L gene of the invention and/or a DNA fragment for use as the specific primer, a method for cancer diagnosis which utilizes them, and a diagnostic kit therefor.

For example, the TSC403 gene probe according to the invention can be produced and acquired by the standard PCR technique using two kinds of primers (sense primer and antisense primer) which are specific to the TSC403 gene of the invention. With the probe thus constructed, expression of the genes of the invention in various neoplastic and other tissues can be detected.

BRIEF DESCRIPTION OF DRAWINGS

FIG. 1 is a photograph substituting for a drawing which shows a distribution of the TSC403 gene of the invention in human tissues as found by the Northern blot analysis in accordance with Example 1-(2).

FIG. 4 is a photograph substituting for a drawing which shows the expression of the TSC403 gene in human tissues as found by the Northern analysis in accordance with Example 1-(5).

FIG. 5 is a photograph substituting for a drawing which shows the expression of the TSC403 gene in human tissues as found by the Northern analysis in accordance with Example

FIG. 8 shows the result of a homology study between the predicted amino acid sequence of the protein encoded by the human ING1L gene of the invention and that of p33$^{ING1}$ [GenBank A. C. No. AF044076].

FIG. 10 is a photograph substituting for a drawing which shows the results of a Northern blot analysis of the colorectal cancer patient tissue in accordance with Example 2-(2).

BEST MODE FOR CARRYING OUT THE INVENTION

Figure 2:
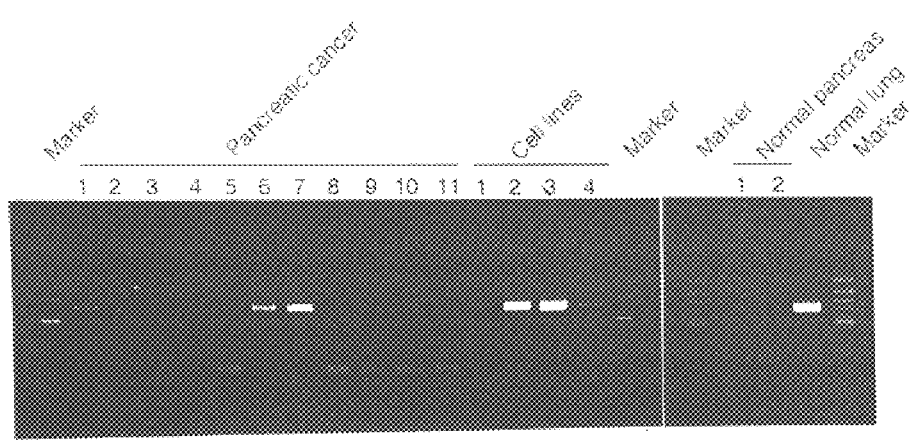
FIG. 2 is a photograph substituting for a drawing which shows the results of the RT-PCR analysis of various normal tissues and cancer tissues in accordance with Example 1-(4).

The following examples are intended to illustrate the invention in further detail.

EXAMPLE 1

TSC403 gene (1-1) Procedure for Imaging by [γ-$^{33}$P]ATP Labeling

For confirmation of the human gene expressed by a tissue-specific technique, the [-$^{33}$P]ATP-labeled imaging method was used. This method was essentially carried out according to the protocol of Liang [Liang P. , et al., Science, 257, 967–971 (1992)].

Thus, the poly A RNA (0.2 µg) isolated from each of 13 human tissues (adult brain, fetal brain, lung, liver, stomach, pancreas, spleen, mammary gland, prostate, placenta, testis, kidney and heart; Clontech) was mixed with 25 pmol of 3'-anchored oligo-dT primer G(T) 15 MA (M stands for a mixture of G, A and C) in 8 µl of diethyl pyrocarbonate-treated water and the mixture was heated at 65° C. for 5 minutes. To this solution, 4 µl of 5×first strand buffer (BRL), 2 µl of 0.1 M DTT (BRL), 1 µl of 250 mM dNTPs (BRL), 1 µl of ribonuclease inhibitor (40 units; Toyobo) and 1 µl of Superscript II reverse transcriptase (200 units; BRL) were added. The final volume of each reaction mixture was 20 µl. Each solution was incubated at 37° C. for 1 hour and diluted 2.5-fold by adding 30 µl of distilled water and the dilution was stored at −20° C. until used.

The cDNA was amplified by PCR in the presence of [γ-$^{33}$P]ATP-labeled (Pharmacia) 3'-anchored primer. This PCR amplification of cDNA was carried out as follows.

Thus, 20 µl of each PCR mixture contained 2 µl of RT reaction mixture, 2 µl of 10×PCR buffer (Takara), 4 µl of 2.5 mM dNTPs, 0.25 µl of ExTaq DNA polymerase (5 U/ml; Takara), 25 pmol of 3'-anchored oligo-dT primer labeled with [α-$^{33}$P]ATP, and 25 pmol of 5'-primer (No. 20, a 10-mer deoxyoligonucleotide primer having a randomized sequence of the sequence SEQ ID NO: 9). The PCR was carried out under the following conditions: one cycle of 95° C. for 3 min., 40° C. for 5 min. and 72° C. for 5 min.; 40 cycles of 95° C. for 0.5 min., 40° C. for 2 min. and 72° C. for 1 min.; and annealing at 72° C. for 5 min.

The PCR sample was extracted with ethanol, resuspended in formamide-sequencing dye, and reacted on the 6% acrylamide-7.5 M urea sequencing gel. The gel was dried without fixing and autoradiography was performed overnight.

(1-2) Sub-cloning of the Amplified cDNA Fragment

A 3 MM filter paper, on which the dry gel was placed in advance, was marked in a radioactive ink and the autoradiogram was set in registry with the marking. The gel containing the objective cDNA band was cut out together with the 3 MM filter paper and stirred in 300 µl of dH$_2$O for 1 hour. After removal of the polyacrylamide gel and filter paper, the cDNA was recovered by ethanol precipitation in the presence of 1 µl of 10 mg/ml glycogen and 0.3 M NaOAc as the carrier and redissolved in 10 µl of dH$_2$O. For reamplification, 5 µl of this solution was used. The PCR conditions and primers used were the same as those used for the first PCR. The reamplification product of a suitable size was recovered as the first PCR product and this PCR product was cloned in the Hinc II site of pUC118 vector (Takara). The nucleic acid sequence was determined by using ABI377 Automatic Sequencer (Applied BioSystems).

By comparing the various image patterns obtained with the mRNAs isolated from 13 kinds of human tissues, one PCR product expressed specifically in the lung could be identified. This product was named TSC403DD.

This product consisted of 252 nucleotides. Comparison of this nucleotide data with the DNA sequences in the GenBank/EMBL Database using FASTA Program [Person, W. R., et al., Proc. Natl. Acad. Sci., USA, 85, 2444–2448 (1988)] revealed that this PCR product has no homology to any known DNA sequence.

(1-3) cDNA Screening

A human normal lung cDNA library was constructed using oligo(dT)+random hexamer-primed human normal lung cDNA and Uni-ZAP™ XR (Stratagene). All the 1×10$^6$ clones were isolated by the above-described procedure and a screening was carried out using the [α-$^{32}$P]-dCTP-labeled cDNA fragment. Positive clones were selected and the cloned sites of cDNA were excised in vivo in pBluescript II SK(−).

As a result, about 100 plaques were identified for said TSC403DD. Based on this result, the transcription amount in the total RNA population was calculated to be about 0.01%.

The assembled cDNA sequence (TSC403) homologous to TSC403DD comprised 3198 nucleotides inclusive of a 1248-nucleotide open reading frame coding for a 416-amino acid residue protein having a calculated molecular mass of 44316 Da.

From the primary sequence, this gene product (TSC403 protein) was found to be a protein containing a transmembrane domain.

Its chromosomal locus was found to be 3q27 where chromosomal aberrations are noted in various kinds of cancers.

Furthermore, the gene TSC403 of the invention has about 30% homology to human lamp-1 and lamp-2.

(2) Expression in Tissues

To delineate the expression profile of TSC403 in tissues, Northern blotting was performed using various human tissues.

In the Northern blot analysis, human MTN (Multiple-Tissue Northern) blot I and II (Clontech) were used. The cDNA fragment was prepared by using a primer set of T3 and T7 promoter sequences and labeled with [α-$^{32}$P]-dCTP by PCR. The membrane containing the amplification product was subjected to the prehybridization (under the conditions of the product protocol) and further to hybridization according to the product protocol.

After hybridization, the membrane was washed and exposed for autoradiography at −80° C. for 24 hours. The results are shown in FIG. 1.

The human tissues used and represented on the drawing are heart, brain, placenta, lung, liver, skeletal muscle, kidney, pancreas, spleen, thymus, prostate, testis, ovary, small intestine, colon and peripheral blood leukocyte; P.B.L.).

As can be seen from the drawing, a transcript homologous to TSC403 was specifically detected in the lung.

(3) FISH

FISH for chromosome mapping was carried out by the known method [Takahashi E., et al., Hum. Genet., 86, 14–16 (1990)] using 0.5 μg of each cosmid DNA as a probe. FISH was caught by Provia 100 film (Fuji; ISO 100) or with a CCD camera system (Applied Imaging, Cyto Vision).

As a result, the 100 signals obtained with the cells in the typical R-band (pro) metaphase were localized in the 3q27 band. Therefore, the chromosomal locus of TSC403 could be identified to be 3q27.

(4) Expression in Cancer Cell Lines and Cancer Tissues as Analyzed by RT-PCR

To investigate whether the expression of the TSC403 gene would be mutated in human cancer cell lines and cancer tissues, four cell lines [Aspc1 (metastatic adenocarcinoma, J. Natl. Cancer Inst., 67, 563–569 (1981)), Bxpc3 (adenocarcinoma, undifferentiated; Cancer Invest., 4, 15–23 (1986)), MiaPaca2 (adenocarcinoma, Int. J. Cancer, 19, 128–135 (1977)) and PANC1 (epithelioid, carcinoma of pancreatic duct, Int. J. Cancer, 15, 741–747 (1975)) and 9 cancer tissues (donated by Dr. Nakamura, The Institute of Medical Science, the University of Tokyo) ] were subjected to RT-PCR analysis.

Thus, 10 μl of the whole RNA isolated from each cell line or cancer tissue by using ISOGEN (Wako Chemical Ind.) was treated with 10 units of RNase-free DNase I (Boehringer Mannheim) for 15 minutes, extracted twice with phenol-chloroform, and precipitated from ethanol. The single-stranded cDNA was synthesized by means of Superscript I$_{TM}$ RNase H-reverse transcriptase (Life Technology) using oligo-(dT) and random primers. A 2 μl-portion of each product was used for PCR amplification.

The primers P1 and P2 having the nucleotide sequences depicted in SEQ ID NO:10 and SEQ ID NO:11 were used for 25-cycle PCR amplification.

The PCR was carried out in 20 μl of a solution of DNA 25 ng, primers 10 μM each, dNTP 2.5 mM and Extaq DNA polymerase (Takara) 0.25 U. The PCR product was dissolved in ethidium bromide-stained 1.5% agarose gel.

The results of the RT-PCR analysis of 4 cell lines (lane 1=AsPc-1, Lane 2=BxPc-3, Lane 3=MIApaca, lane 4=PANC-1), normal pancreatic tissue (Normal pancreas, lanes 1and 2), pancreatic cancer tissue (Pancreatic cancer, lanes 1–11) and normal lung tissue (Normal lung) by the above procedure are shown in FIG. 2.

It is clear from FIG. 2 that the expression of TSC403 was not found in the normal pancreatic tissue (Normal pancreas, lanes 1 and 2) but found exclusively in the pancreatic cancer tissue (Pancreatic cancer, lanes 1–11 and Cell lines, lanes 1–4).

Incidentally, the 4 cell lines used above have been deposited with ATCC and their accession numbers are as follows.

Aspc-1; CRL-1682

BxPc-3; CRL-1687

MIApaca; CRL-1420

PANC-1; CRL-1469

(5) Expression of the TSC403 Gene in Various Cancers (Northern Blot Analysis)

Expression of the TSC403 gene was studied by hybridizing the TSC403 gene to the blot (Invitrogen carrying the following various cancer tissue and normal tissue mRNA samples (tumor Northern blot analysis). All the cancer tissues and normal tissues used were purchased from Invitrogen.

Figure 3:
FIG. 3 is a photograph substituting for a drawing which shows the expression of the TSC403 gene in human tissues as found by the Northern analysis in accordance with Example 1-(5).
Figure 3:

The results are shown in FIG. 3, FIG. 4 and FIG. 5. The cancer tissues and normal tissues represented on each drawing are as follows.

FIG. 3:

Brain tumor, brain normal, kidney tumor, kidney normal, liver tumor, liver normal, lung tumor, lung normal, breast tumor, normal breast, uterine tumor, normal uterine, fallopian tube tumor, normal fallopian tube, ovarian tumor, normal ovary.

FIG. 4:

Esophagus tumor, normal esophagus, stomach tumor, normal stomach, colon tumor, normal colon, rectum tumor, normal rectum, thyroid tumor, normal thyroid, adrenal tumor, normal adrenal, parotid tumor, normal parotid, lymphoma, normal lymph node.

FIG. 5:

Kidney tumor, normal kidney, ureter tumor, normal ureter, bladder tumor, normal bladder, stomach tumor, normal stomach, ovarian tumor (4 cases), ovarian normal (4 cases).

From the above drawings, significant expression of TSC403 can be found in the normal lung. In addition, expression of the TSC403 gene was observed in breast tumor (FIG. 3), fallopian tube tumor (FIG. 3), esophagus tumor (FIG. 4), colon tumor (FIG. 4), rectum tumor (FIG. 4), thyroid tumor (FIG. 4), parotid tumor (FIG. 4), ureter tumor (FIG. 5), ovarian tumor (FIG. 5, 2 out of 4 cases).

(6) Focus forming Assay by Expression of the TSC403 Gene

The full-length open reading frame of the TSC403 gene was ligated to the BamHI-XhoI site of the pCDNA 3.1/His (Invitrogen) vector to obtain a TSC403 gene expression vector.

Then, using the expression vector obtained above, a focus forming assay using NIH3T3 cells was carried out according to the method described in the literature [Shin, C., Shilo, B., Goldfarb, M. P., et al., Proc. Natl. Acad. Sci., USA., 76, 5714–5718 (1979)] to see whether the TSC403 gene has a tumorigenic effect on cells.

Figure 6:
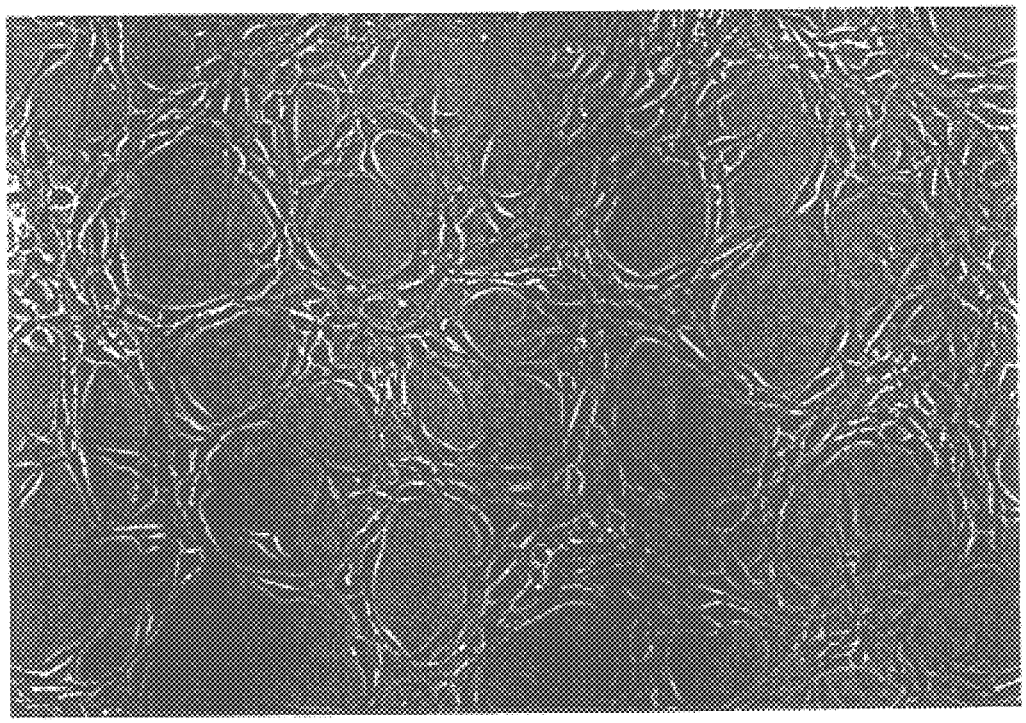
FIG. 6 is a photograph substituting for a drawing which shows control cells in the focus forming test in accordance with Example 1-(6).
Figure 7:
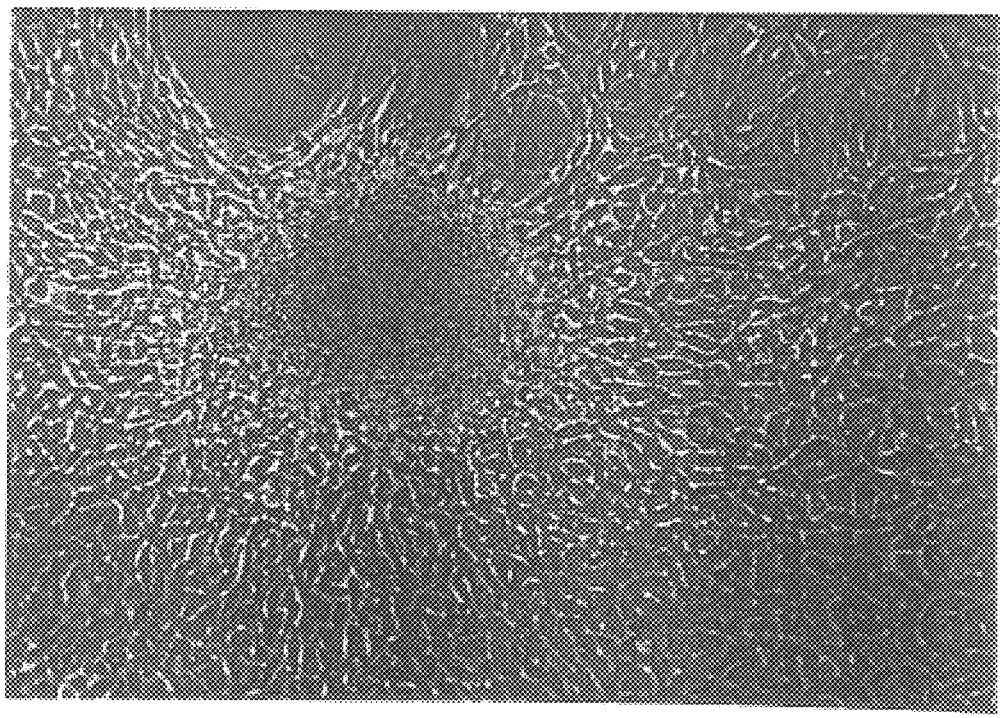
FIG. 7 is a photograph substituting for a drawing which shows transformant cells as transformed with the TSC403 gene of the invention in the focus forming test in accordance with Example 1-(6).

The results are shown in FIG. 6 (control cells not transformed with TSC403 gene) and FIG. 7 (cells transformed with TSC403 gene).

As is apparent from comparison of the two figures, a definite focus was formed, as shown in FIG. 7, when the TSC403 gene was force-expressed in cells by introduction of the gene. It is, thus, apparent that the TSC403 gene, when over-expressed by force, causes a loss of sensitivity to the contact inhibition phenomenon which is one of malignant transformations of cells, thus being deeply involved in the tumorigenesis of cells.

EXAMPLE 2

Human ING1L gene (1) Cloning and DNA Sequencing of the Human ING1L Gene

By the sequencing of cDNA clones arbitrarily selected from a human fetal brain cDNA library and database search, one clone (GEN-146F11) harboring a cDNA coding for an amino acid sequence having high homology to p33$^{ING1}$, a protein considered to be a tumor-suppressive protein, was isolated by the following procedure.

Thus, the mRNA extracted from human fetal brain was purchased from Clontech and used as the starting material. From the mRNA, the cDNA was synthesized and cloned into Vector λZAPII (Stratagene) to construct a cDNA library (Otsuka GEN Research Institute, Otsuka Pharmaceutical). By the in vivo excision method [Short, J. M. et al., Nucleic Acids Res., 16, 7583–7600 (1988)], colonies of *Escherichia coli* harboring the human gene were caused to form on agar medium and picked up at random and *E. coli* clones harboring the human gene were registered on a 96 -well microtiter plate. The registered clones were stored at −80° C.

Then, each registered clone was cultured in 1.5 ml of LB medium for 24 hours, and using a plasmid automatic extractor PI-100 (Kurabo), the DNA was extracted and purified. The contaminated *E. coli* RNA was decomposed by RNase treatment and removed. Finally, the DNA was dissolved to 30 μl and a 2 μl portion was used for a rough estimation of DNA size and amount by the minigel method. Another 7 portion was used for sequencing reaction and the remaining 21 μl portion was stored as plasmid DNA at 4° C.

Then, a Sanger's dideoxy terminator [Sanger, F., et al., Proc. Natl. Acad. Sci., U.S.A., 74, 5463–5467 (1977)] using T3, T7 or a synthetic oligonucleotide primer or a cycle sequencing method which is the dideoxy terminator method combined with the PCR method [Carothers, A. M., et al., Bio. Techniques, 7, 494–499 (1989)] was carried out. These are the methods for chain extension reaction with termination specific to 4 kinds of bases using a small amount of plasmid DNA (ca 0.1–0.5 g) as a template.

Using an FITC (fluorescein isothiocyanate)-labeled primer as the sequence primer, about 25 cycles of reaction using Taq polymerase were carried out. Of the fluorescence-labeled DNA fragment, the sequence of about 400 nucleotides from the 5'-end of the cDNA was determined with the automatic DNA sequencer ALF™ DNA Sequencer (Pharmacia).

The 3'-nontranslated region is high in heterogeneity among genes and suited for differentiation of individual genes. Therefore, sequencing of the 3'-end region was also performed in some cases.

The huge nucleotide sequence information generated with the DNA sequencer was transmitted to the 64-bit computer DEC3400 for computerized homology analysis. This homology analysis was carried out by a database (GenBank, EMBL) search according to UWGCG's FASTA Program [Pearson, W. R. and Lipman, D. J., Proc. Natl. Acad. Sci., USA., 85, 2444–2448 (1988)].

The above method of analysis for a human fetal brain cDNA library is described in detail by Fujiwara et al. [Fujiwara, T., et al., DNA Res., 2, 107–111 (1991)].

About 5040 ESTs (expressed sequence tags: partial DNA sequences of expressed gene fragment) randomly selected from the human fetal brain cDNA library constructed as above were then sequenced.

The clone named GEN-146F11 in the GenBank/EMBL sequence search according to the FASTA Program was found to harbor a gene coding for an amino acid sequence having high homology to p33$^{ING1}$ [GenBank A. C. No. AF001954].

To clarify the full-length sequence in said GEN-146F11 clone, a DNA sequencing reaction using T7DNA polymerase and a synthetic primer was carried out. In addition, using a double-stranded DNA inserted into a vector (pBluescript vector; Stratagene) as a template and a synthetic oligonucleotide as a primer, the nucleotide sequence of the cDNA inclusive of the whole coding region was determined by Sanger's dideoxy chain termination method, and the sequence was compared with the DNA sequences of several other related genes.

SEQ ID NO:7 shows the nucleic acid sequence of GEN-146F11 clone (cDNA); SEQ ID NO:6 shows the nucleic acid sequence of the coding region of said clone; and SEQ ID NO:5 shows the deduced amino acid sequence encoded by said nucleic acid sequence.

In the above nucleotide sequences, the initiation signal sequence was found in the position 92–94and suspected to be the translation start codon. The predicted stop codon was found in the position 932–934.

The cDNA has a length of 1078 nucleotides and contained an open reading frame of 840 base pairs that coded for a predicted 280-amino acid residue protein.

By the homology search using FASTA Program, this gene was found to code an amino acid sequence having high homology to p33$^{ING1}$ [GenBank A. C. No. AF044076]. The homology of the nucleotide sequence was 60.0%.

On the amino acid sequence level, the homology between the deduced amino acid sequence of the protein encoded by the gene of the invention and the sequence of p33$^{ING1}$ [GenBank A. C. No. AF044076] was investigated. The result is shown in FIG. 8.

Figure 8:
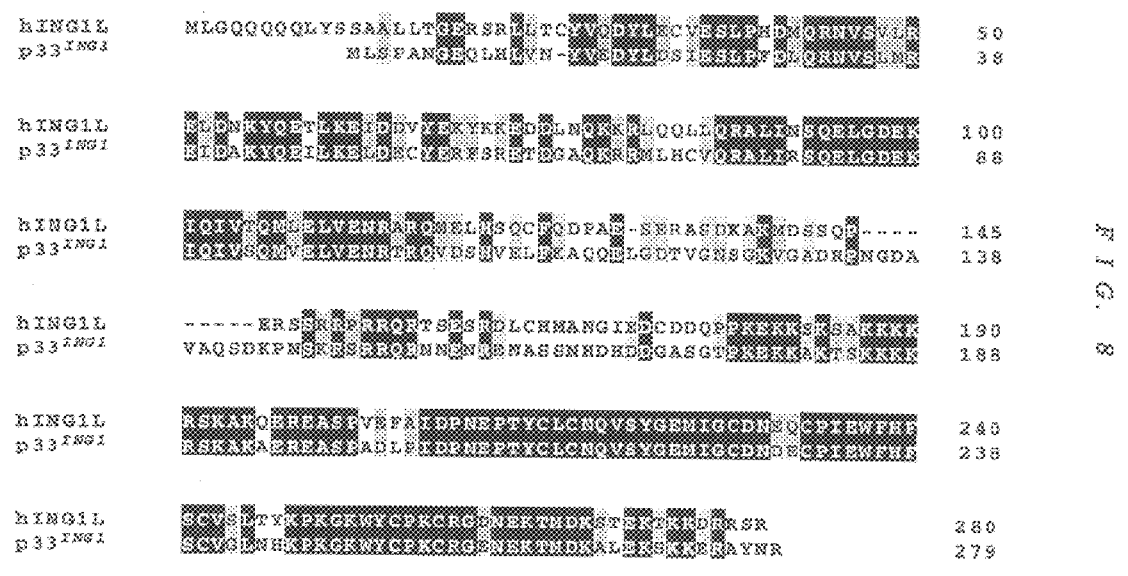

FIG. 8 shows the amino acid sequence depicted in single letters; the top row represents the sequence of the human ING1L protein encoded by the gene of the invention (indicated as hING1L) and the bottom row represents the sequence of p33$^{ING1}$ [Garkavetsev, et al., Nature. Genet., 14, 415–420 (1996); Garkavetsev, etal., Mol. Cell. Biol., 17, 2014–2019 (1997), GenBank A. C. No. AF001954; however this sequence has been revised subsequently and the sequence as corrected is shown in GenBank A. C. No. AF044076; indicated as p33$^{ING1}$ on the drawing].

Furthermore, on the same drawing, the solid area (black frame) indicates the identical amino acid residues and the shaded area (shaded frame) indicates analogous amino acid residues. The symbol - - - in the hING1L row stands for a gap.

It can be seen from the drawing that the amino acid sequence encoded by the gene of the invention has 58.9% (as calculated based on the sequence as corrected of p33$^{ING1}$) homology to the amino acid sequence of p33$^{ING1}$.

(2) Northern Blot Analysis

The expression of human ING1L mRNA in normal human tissues was evaluated by Northern blotting using a human cDNA clone labeled by the random oligonucleotide priming method as a probe.

The Northern blot analysis was performed using a human MTN blot (Human Multiple Tissue Northern Blot; Clontech) according to the product protocol.

Thus, the full-length sequence of said clone GEN-146F11 was PCR-amplified and the PCR product was labeled with [$^{32}$P]-dCTP (Random Primed DNA Labeling Kit, Boehringer Mannheim) for use as a probe.

The blot was subjected to 4-hour prehybridization and, then, to hybridization in a solution of 50% formamide/5× SSC/10×Decherd solution/2% SDS solution (containing 100 μg/ml of denatured salmon sperm DNA) at 42° C. overnight. After two washings with 2×SSC/0.1% SDS at room temperature, 2 washings were carried out with 0.2×SSC/ 0.1% SDS at 65° C. for 15 minutes. The filter was exposed against X-ray film (Kodak) at −70° C.

Figure 9:
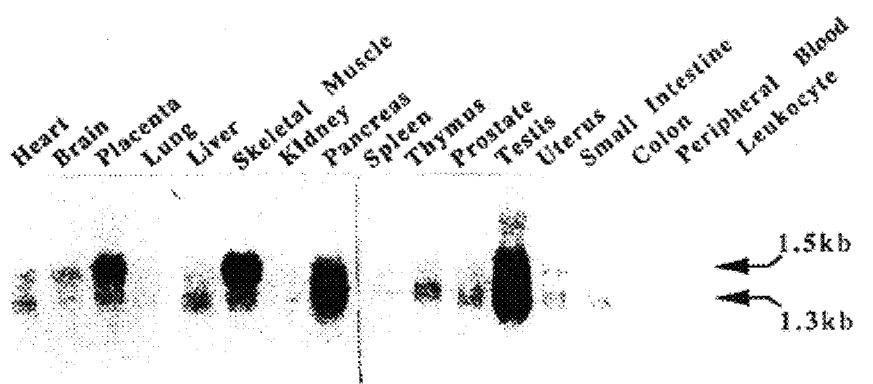
FIG. 9 is a photograph substituting for a drawing which shows the results of a Northern blot analysis of 16 human adult organ-derived cells in accordance with Example 2-(2).

The results of 18-hour exposure are shown in FIG. 9.

As can be seen in FIG. 9, the expression was found in all the 16 human adult organ-derived tissues tested (heart, brain, placenta, lung, liver, skeletal muscle, kidney, pancreas, spleen, thymus, prostate, testis, uterus, small intestine, colon, peripheral blood and leukocyte; the same nomenclature applies to the legends on the drawing), and two transcripts of 1.5 kb and 1.3 kb were detected.

Furthermore, for the several tumor tissues of colorectal cancer, cancer of esophagus, cancer of uterine tube and stomach cancer, too, a similar Northern blot analysis was carried out using a human TP blot (Human Tumor Panel Blot; Invitrogen) in accordance with the product protocol.

The results in colorectal cancer patient tissues are shown in FIG. 10.

On the drawing, T represents the colorectal tumor tissue (indicated as T:Tumor on the drawing) and N represents the normal colorectal tissue (indicated as N:Normal on the drawing). One set of T and N is the tissue derived from one patient and the drawing shows the results for tissues derived from 4 patients.

It is clear from the drawing that in each individual patient, the level of expression of the human ING1L gene is elevated in the cancerous tissue as compared with the normal tissue.

Based on the above findings, it is thought that the human ING1L gene of the invention is useful for cancer research and therapy, particularly for application to cancer diagnosis, and that if any antagonistic inhibitor of expression products of the human ING1L gene be developed in the future, it should find application as an anticancer agent.

(3) Chromosome Mapping by FISH and Radiation Hybridizing Techniques

FISH for chromosome alignment was carried out by the known procedure [Takahashi, E. et al., Hum. Genet., 86, 14–16 (1990)] using 0.5 μg of each cosmid DNA as a probe. FISH was caught by Provia 100 film (Fuji, ISO 100) or with a CCD Camera System (Applied Imaging, Cyto Vision).

As a result, signals of 100 typical R-band (pro) metaphase cells indicated that the locus of the human ING1L gene on a chromosome was 4q35.1.

INDUSTRIAL APPLICABILITY

In accordance with the invention, there is provided not only a novel lung-specific gene TSC403 but also a protein encoded thereby. Through utilization thereof, there is provided a technology by which more light may be cast on cancers, e.g. lung cancer and pancreatic cancer, and the process of oncogenesis and which finds application in the diagnosis, prophylaxis and therapy thereof.

Further provided in accordance with the invention is a novel human ING1L gene which enables detection of the expression of the gene in various tissues, production of a human ING1L protein, which is the expression product of the gene, by genetic engineering technology, and construction of a specific antibody against said protein. These, in turn, enable research into the cell cycle, inhibition of growth or activation of various cells, study of metabolic aging and apoptosis of cells, and exploration, treatment or diagnosis of related diseases such as cancers, as mentioned hereinbefore. In addition, the invention enables the development of, or screening for, antagonistic inhibitors of said human ING1L protein, namely cell growth suppressants and anticancer drugs.

What is claimed is:

1. An isolated DNA molecule comprising nucleotides 1 to 1248 of SEQ ID NO. 2.

2. The isolated DNA molecule of claim 1, wherein said DNA molecule encodes a TSC403 polypeptide comprising amino acids 1-416 of SEQ ID NO: 1.

* * * * *

SEQUENCE LISTING

<160> NUMBER OF SEQ ID NOS:  11

<210> SEQ ID NO 1
<211> LENGTH: 416
<212> TYPE: PRT
<213> ORGANISM: Homo sapiens
<220> FEATURE:
<223> OTHER INFORMATION: Human normal lung cDNA  library

<400> SEQUENCE: 1

```
Met Pro Arg Gln Leu Ser Ala Ala Ala L eu Phe Ala Ser Leu Ala
 1               5                  10                  15

Val Ile Leu His Asp Gly Ser Gln Met Arg A la Lys Ala Phe Pro Glu
            20                  25                  30

Thr Arg Asp Tyr Ser Gln Pro Thr Ala Ala A la Thr Val Gln Asp Ile
        35                  40                  45

Lys Lys Pro Val Gln Gln Pro Ala Lys Gln A la Pro His Gln Thr Leu
    50                  55                  60

Ala Ala Arg Phe Met Asp Gly His Ile Thr P he Gln Thr Ala Ala Thr
65                  70                  75                  80

Val Lys Ile Pro Thr Thr Thr Pro Ala Thr T hr Lys Asn Thr Ala Thr
                85                  90                  95

Thr Ser Pro Ile Thr Tyr Thr Leu Val Thr T hr Gln Ala Thr Pro Asn
            100                 105                 110

Asn Ser His Thr Ala Pro Pro Val Thr Glu V al Thr Val Gly Pro Ser
        115                 120                 125

Leu Ala Pro Tyr Ser Leu Pro Pro Thr Ile T hr Pro Pro Ala His Thr
```

```
                  130                 135                 140
Ala Gly Thr Ser Ser Ser Thr Val Ser His Thr Thr Gly Asn Thr Thr
145                 150                 155                 160

Gln Pro Ser Asn Gln Thr Thr Leu Pro Ala Thr Leu Ser Ile Ala Leu
                165                 170                 175

His Lys Ser Thr Thr Gly Gln Lys Pro Asp Gln Pro Thr His Ala Pro
            180                 185                 190

Gly Thr Thr Ala Ala His Asn Thr Thr Arg Thr Ala Ala Pro Ala
        195                 200                 205

Ser Thr Val Pro Gly Pro Thr Leu Ala Pro Gln Pro Ser Ser Val Lys
        210                 215                 220

Thr Gly Ile Tyr Gln Val Leu Asn Gly Ser Arg Leu Cys Ile Lys Ala
225                 230                 235                 240

Glu Met Gly Ile Gln Leu Ile Val Gln Asp Lys Glu Ser Val Phe Ser
                245                 250                 255

Pro Arg Arg Tyr Phe Asn Ile Asp Pro Asn Ala Thr Gln Ala Ser Gly
            260                 265                 270

Asn Cys Gly Thr Arg Lys Ser Asn Leu Leu Leu Asn Phe Gln Gly Gly
        275                 280                 285

Phe Val Asn Leu Thr Phe Thr Lys Asp Glu Glu Ser Tyr Tyr Ile Ser
        290                 295                 300

Glu Val Gly Ala Tyr Leu Thr Val Ser Asp Pro Glu Thr Val Tyr Gln
305                 310                 315                 320

Gly Ile Lys His Ala Val Val Met Phe Gln Thr Ala Val Gly His Ser
                325                 330                 335

Phe Lys Cys Val Ser Glu Gln Ser Leu Gln Leu Ser Ala His Leu Gln
            340                 345                 350

Val Lys Thr Thr Asp Val Gln Leu Gln Ala Phe Asp Phe Glu Asp Asp
        355                 360                 365

His Phe Gly Asn Val Asp Glu Cys Ser Ser Asp Tyr Thr Ile Val Leu
    370                 375                 380

Pro Val Ile Gly Ala Ile Val Val Gly Leu Cys Leu Met Gly Met Gly
385                 390                 395                 400

Val Tyr Lys Ile Arg Leu Arg Cys Gln Ser Ser Gly Tyr Gln Arg Ile
                405                 410                 415
```

<210> SEQ ID NO 2
<211> LENGTH: 1248
<212> TYPE: DNA
<213> ORGANISM: Homo sapiens
<220> FEATURE:
<223> OTHER INFORMATION: human normal lung cDNA library

<400> SEQUENCE: 2

```
atgccccggc agctcagcgc ggcggccgcg ctcttcgcgt ccctggccgt a attttgcac     60
gatggcagtc aaatgagagc aaaagcattt ccagaaacca gagattattc t caacctact    120
gcagcagcaa cagtacagga cataaaaaaa cctgtccagc aaccagctaa g caagcacct    180
caccaaactt tagcagcaag attcatggat ggtcatatca cctttcaaac a gcggccaca    240
gtaaaaattc aacaactac cccagcaact acaaaaaaca ctgcaaccac c agcccaatt    300
acctacaccc tggtcacaac ccaggccaca cccaacaact cacacacagc t cctccagtt    360
actgaagtta cagtcggccc tagcttagcc ccttattcac tgccacccac c atcacccca    420
ccagctcata cagctggaac cagttcatca accgtcagcc acacaactgg g aacaccact    480
```

-continued

```
caacccagta accagaccac ccttccagca actttatcga tagcactgca c aaaagcaca      540 accggtcaga agcctgatca acccacccat gccccaggaa caacggcagc t gcccacaat      600 accacccgca cagctgcacc tgcctccacg gttcctgggc caccccttgc a cctcagcca     660 tcgtcagtca agactggaat ttatcaggtt ctaaacggaa gcagactctg t ataaaagca     720 gagatgggga tacagctgat tgttcaagac aaggagtcgg ttttttcacc t cggagatac     780 ttcaacatcg accccaacgc aacgcaagcc tctgggaact gtggcacccg a aaatccaac     840 cttctgttga attttcaggg cggatttgtg aatctcacat ttaccaagga t gaagaatca     900 tattatatca gtgaagtggg agcctatttg accgtctcag atccagagac a gtttaccaa     960 ggaatcaaac atgcggtggt gatgttccag acagcagtcg ggcattcctt c aagtgcgtg    1020 agtgaacaga gcctccagtt gtcagcccac ctgcaggtga aaacaaccga t gtccaactt    1080 caagcctttg attttgaaga tgaccacttt ggaaatgtgg atgagtgctc g tctgactac    1140 acaattgtgc ttcctgtgat tggggccatc gtggttggtc tctgccttat g ggtatgggt    1200 gtctataaaa tccgcctaag gtgtcaatca tctggatacc agagaatc                  1248
```

<210> SEQ ID NO 3
<211> LENGTH: 3198
<212> TYPE: DNA
<213> ORGANISM: Homo sapiens
<220> FEATURE:
<223> OTHER INFORMATION: human normal lung cDNA library
<221> NAME/KEY: CDS
<222> LOCATION: (64)..(1311)

<400> SEQUENCE: 3

```
ggcaccgatt cggggcctgc ccggacttcg ccgcacgctg cagaacctcg c ccagcgccc      60 acc atg ccc cgg cag ctc agc gcg gcg gcc g cg ctc ttc gcg tcc ctg      108
    Met Pro Arg Gln Leu Ser Ala Ala Ala Leu Phe Ala Ser Leu
    1               5                   10                  15 gcc gta att ttg cac gat ggc agt caa atg a ga gca aaa gca ttt cca      156
Ala Val Ile Leu His Asp Gly Ser Gln Met A rg Ala Lys Ala Phe Pro
                20                  25                  30 gaa acc aga gat tat tct caa cct act gca g ca gca aca gta cag gac      204
Glu Thr Arg Asp Tyr Ser Gln Pro Thr Ala A la Ala Thr Val Gln Asp
        35                  40                  45 ata aaa aaa cct gtc cag caa cca gct aag c aa gca cct cac caa act      252
Ile Lys Lys Pro Val Gln Gln Pro Ala Lys G ln Ala Pro His Gln Thr
    50                  55                  60 tta gca gca aga ttc atg gat ggt cat atc a cc ttt caa aca gcg gcc      300
Leu Ala Ala Arg Phe Met Asp Gly His Ile T hr Phe Gln Thr Ala Ala
65                  70                  75 aca gta aaa att cca aca act acc cca gca a ct aca aaa aac act gca      348
Thr Val Lys Ile Pro Thr Thr Thr Pro Ala T hr Thr Lys Asn Thr Ala
80                  85                  90                  95 acc acc agc cca att acc tac acc ctg gtc a ca acc cag gcc aca ccc      396
Thr Thr Ser Pro Ile Thr Tyr Thr Leu Val T hr Thr Gln Ala Thr Pro
                100                 105                 110 aac aac tca cac aca gct cct cca gtt act g aa gtt aca gtc ggc cct      444
Asn Asn Ser His Thr Ala Pro Pro Val Thr G lu Val Thr Val Gly Pro
        115                 120                 125 agc tta gcc cct tat tca ctg cca ccc acc a tc acc cca cca gct cat      492
Ser Leu Ala Pro Tyr Ser Leu Pro Pro Thr I le Thr Pro Pro Ala His
    130                 135                 140 aca gct gga acc agt tca tca acc gtc agc c ac aca act ggg aac acc      540
Thr Ala Gly Thr Ser Ser Ser Thr Val Ser H is Thr Thr Gly Asn Thr
145                 150                 155
```

-continued

| | |
|---|---|
| act caa ccc agt aac cag acc acc ctt cca g ca act tta tcg ata gca<br>Thr Gln Pro Ser Asn Gln Thr Thr Leu Pro A la Thr Leu Ser Ile Ala<br>160     165     170     175 | 588 |
| ctg cac aaa agc aca acc ggt cag aag cct g at caa ccc acc cat gcc<br>Leu His Lys Ser Thr Thr Gly Gln Lys Pro A sp Gln Pro Thr His Ala<br>     180     185     190 | 636 |
| cca gga aca acg gca gct gcc cac aat acc a cc cgc aca gct gca cct<br>Pro Gly Thr Thr Ala Ala Ala His Asn Thr T hr Arg Thr Ala Ala Pro<br>   195     200     205 | 684 |
| gcc tcc acg gtt cct ggg ccc acc ctt gca c ct cag cca tcg tca gtc<br>Ala Ser Thr Val Pro Gly Pro Thr Leu Ala P ro Gln Pro Ser Ser Val<br>210     215     220 | 732 |
| aag act gga att tat cag gtt cta aac gga a gc aga ctc tgt ata aaa<br>Lys Thr Gly Ile Tyr Gln Val Leu Asn Gly S er Arg Leu Cys Ile Lys<br>   225     230     235 | 780 |
| gca gag atg ggg ata cag ctg att gtt caa g ac aag gag tcg gtt ttt<br>Ala Glu Met Gly Ile Gln Leu Ile Val Gln A sp Lys Glu Ser Val Phe<br>240     245     250     255 | 828 |
| tca cct cgg aga tac ttc aac atc gac ccc a ac gca acg caa gcc tct<br>Ser Pro Arg Arg Tyr Phe Asn Ile Asp Pro A sn Ala Thr Gln Ala Ser<br>     260     265     270 | 876 |
| ggg aac tgt ggc acc cga aaa tcc aac ctt c tg ttg aat ttt cag ggc<br>Gly Asn Cys Gly Thr Arg Lys Ser Asn Leu L eu Leu Asn Phe Gln Gly<br>   275     280     285 | 924 |
| gga ttt gtg aat ctc aca ttt acc aag gat g aa gaa tca tat tat atc<br>Gly Phe Val Asn Leu Thr Phe Thr Lys Asp G lu Glu Ser Tyr Tyr Ile<br>     290     295     300 | 972 |
| agt gaa gtg gga gcc tat ttg acc gtc tca g at cca gag aca gtt tac<br>Ser Glu Val Gly Ala Tyr Leu Thr Val Ser A sp Pro Glu Thr Val Tyr<br>305     310     315 | 1020 |
| caa gga atc aaa cat gcg gtg gtg atg ttc c ag aca gca gtc ggg cat<br>Gln Gly Ile Lys His Ala Val Val Met Phe G ln Thr Ala Val Gly His<br>320     325     330     335 | 1068 |
| tcc ttc aag tgc gtg agt gaa cag agc ctc c ag ttg tca gcc cac ctg<br>Ser Phe Lys Cys Val Ser Glu Gln Ser Leu G ln Leu Ser Ala His Leu<br>     340     345     350 | 1116 |
| cag gtg aaa aca acc gat gtc caa ctt caa g cc ttt gat ttt gaa gat<br>Gln Val Lys Thr Thr Asp Val Gln Leu Gln A la Phe Asp Phe Glu Asp<br>   355     360     365 | 1164 |
| gac cac ttt gga aat gtg gat gag tgc tcg t ct gac tac aca att gtg<br>Asp His Phe Gly Asn Val Asp Glu Cys Ser S er Asp Tyr Thr Ile Val<br>370     375     380 | 1212 |
| ctt cct gtg att ggg gcc atc gtg gtt ggt c tc tgc ctt atg ggt atg<br>Leu Pro Val Ile Gly Ala Ile Val Val Gly L eu Cys Leu Met Gly Met<br>385     390     395 | 1260 |
| ggt gtc tat aaa atc cgc cta agg tgt caa t ca tct gga tac cag aga<br>Gly Val Tyr Lys Ile Arg Leu Arg Cys Gln S er Ser Gly Tyr Gln Arg<br>400     405     410     415 | 1308 |
| atc taattgttgc ccgggggggaa tgaaaataat ggaatttaga gaactcttt tc<br>Ile | 1361 |
| atcccttcca ggatggatgt tgggaaattc cctcagagtg tgggtccttc a acaatgta | 1421 |
| aaccaccatc ttctattcaa atgaagtgag tcatgtgtga tttaagttca g gcagcacat | 1481 |
| caatttctaa atacttttg tttatttat gaaagatata gtgagctgtt t attttctag | 1541 |
| tttccttag aatatttag ccactcaaag tcaacatttg agatatgttg a attaacata | 1601 |
| atatatgtaa agtagaataa gccttcaaat tataaaccaa gggtcaattg t aactaatac | 1661 |
| tactgtgtgt gcattgaaga ttttatttta cccttgatct taacaaagcc t ttgctttgt | 1721 |

-continued

```
tatcaaatgg actttcagtg cttttactat ctgtgtttta tggtttcatg t aacatacat   1781
attcctggtg tagcacttaa ctccttttcc actttaaatt tgttttttgtt t tttgagacg   1841
gagtttcact cttgtcaccc aggctggagt acagtggcac gatctcggct t atggcaacc   1901
tccgcctccc gggttcaagt gattctcctg cttcagcttc ccgagtagct g ggattacag   1961
gcacacacta ccacgcctgg ctaattttttg tattttttatt atagacgggt t tcaccatgt   2021
tggccagact ggtcttgaac tcttgacctc aggtgatcca cccacctcag c ctcccaaag   2081
tgctgggatt acaggcatga gccattgcgc ccggccttaa atgtttttt t aatcatcaa   2141
aaagaacaac atatctcagg ttgtctaagt gtttttatgt aaaccaaca a aagaacaa   2201
atcagcttat atttttttatc ttgatgactc ctgctccaga atgctagact a agaattagg   2261
tggctacaga tggtagaact aaacaataag caagagacaa taataatggc c cttaattat   2321
taacaaagtg ccagagtcta ggctaagcac tttatctata tctcatttca t tctcacaac   2381
ttataagtga atgagtaaac tgagacttaa gggaactgaa tcacttaaat g tcacctggc   2441
taactgatgg cagagccaga gcttgaattc atgttggtct gacatcaagg t ctttggtct   2501
tctccctaca ccaagttacc tacaagaaca atgacaccac actctgcctg a aggctcaca   2561
cctcatacca gcatacgctc accttacagg gaaatgggtt tatccaggat c atgagacat   2621
tagggtagat gaaaggagag ctttgcagat aacaaaatag cctatcctta a taaatcctc   2681
cactctctgg aaggagactg aggggctttg taaaacatta gtcagttgct c attttttatg   2741
ggattgctta gctgggctgt aaagatgaag gcatcaaata aactcaaagt a tttttaaat   2801
ttttttgata atagagaaac ttcgctaacc aactgttctt tcttgagtgt a tagccccat   2861
cttgtggtaa cttgctgctt ctgcacttca tatccatatt tcctattgtt c actttattc   2921
tgtagagcag cctgccaaga atttttatttc tgctgttttt tttgctgcta a agaaaggaa   2981
ctaagtcagg atgttaacag aaaagtccac ataaccctag aattcttagt c aaggaataa   3041
ttcaagtcag cctagagacc atgttgactt tcctcatgtg tttccttatg a ctcagtaag   3101
ttggcaaggt cctgacttta gtcttaataa acattgaat tgtagtaaag g tttttgcaa   3161
taaaaactta ctttggaaaa aaaaaaaaaa aaaaaaa                              3198
```

<210> SEQ ID NO 4
<211> LENGTH: 416
<212> TYPE: PRT
<213> ORGANISM: Homo sapiens
<223> OTHER INFORMATION: human normal lung cDNA library

<400> SEQUENCE: 4

```
Met Pro Arg Gln Leu Ser Ala Ala Ala L eu Phe Ala Ser Leu Ala
 1               5                  10                  15

Val Ile Leu His Asp Gly Ser Gln Met Arg A la Lys Ala Phe Pro Glu
            20                  25                  30

Thr Arg Asp Tyr Ser Gln Pro Thr Ala A la Thr Val Gln Asp Ile
        35                  40                  45

Lys Lys Pro Val Gln Gln Pro Ala Lys Gln A la Pro His Gln Thr Leu
    50                  55                  60

Ala Ala Arg Phe Met Asp Gly His Ile Thr P he Gln Thr Ala Thr
65                  70                  75                  80

Val Lys Ile Pro Thr Thr Thr Pro Ala Thr T hr Lys Asn Thr Ala Thr
                85                  90                  95

Thr Ser Pro Ile Thr Tyr Thr Leu Val Thr T hr Gln Ala Thr Pro Asn
```

```
                100             105             110
Asn Ser His Thr Ala Pro Pro Val Thr Glu Val Thr Val Gly Pro Ser
            115             120             125
Leu Ala Pro Tyr Ser Leu Pro Thr Ile Thr Pro Pro Ala His Thr
            130             135             140
Ala Gly Thr Ser Ser Thr Val Ser His Thr Thr Gly Asn Thr Thr
145             150             155             160
Gln Pro Ser Asn Gln Thr Thr Leu Pro Ala Thr Leu Ser Ile Ala Leu
            165             170             175
His Lys Ser Thr Thr Gly Gln Lys Pro Asp Gln Pro Thr His Ala Pro
            180             185             190
Gly Thr Thr Ala Ala His Asn Thr Thr Arg Thr Ala Ala Pro Ala
            195             200             205
Ser Thr Val Pro Gly Pro Thr Leu Ala Pro Gln Pro Ser Ser Val Lys
            210             215             220
Thr Gly Ile Tyr Gln Val Leu Asn Gly Ser Arg Leu Cys Ile Lys Ala
225             230             235             240
Glu Met Gly Ile Gln Leu Ile Val Gln Asp Lys Glu Ser Val Phe Ser
            245             250             255
Pro Arg Arg Tyr Phe Asn Ile Asp Pro Asn Ala Thr Gln Ala Ser Gly
            260             265             270
Asn Cys Gly Thr Arg Lys Ser Asn Leu Leu Leu Asn Phe Gln Gly Gly
            275             280             285
Phe Val Asn Leu Thr Phe Thr Lys Asp Glu Glu Ser Tyr Tyr Ile Ser
            290             295             300
Glu Val Gly Ala Tyr Leu Thr Val Ser Asp Pro Glu Thr Val Tyr Gln
305             310             315             320
Gly Ile Lys His Ala Val Val Met Phe Gln Thr Ala Val Gly His Ser
            325             330             335
Phe Lys Cys Val Ser Glu Gln Ser Leu Gln Leu Ser Ala His Leu Gln
            340             345             350
Val Lys Thr Thr Asp Val Gln Leu Gln Ala Phe Asp Phe Glu Asp Asp
            355             360             365
His Phe Gly Asn Val Asp Glu Cys Ser Ser Asp Tyr Thr Ile Val Leu
            370             375             380
Pro Val Ile Gly Ala Ile Val Val Gly Leu Cys Leu Met Gly Met Gly
385             390             395             400
Val Tyr Lys Ile Arg Leu Arg Cys Gln Ser Ser Gly Tyr Gln Arg Ile
            405             410             415
```

<210> SEQ ID NO 5
<211> LENGTH: 280
<212> TYPE: PRT
<213> ORGANISM: Homo sapiens
<220> FEATURE:
<223> OTHER INFORMATION: human embryonic brain cDNA library

<400> SEQUENCE: 5

```
Met Leu Gly Gln Gln Gln Gln Leu Tyr Ser Ser Ala Ala Leu Leu
 1               5              10              15
Thr Gly Glu Arg Ser Arg Leu Leu Thr Cys Tyr Val Gln Asp Tyr Leu
            20              25              30
Glu Cys Val Glu Ser Leu Pro His Asp Met Gln Arg Asn Val Ser Val
            35              40              45
Leu Arg Glu Leu Asp Asn Lys Tyr Gln Glu Thr Leu Lys Glu Ile Asp
```

```
        50                  55                  60
Asp Val Tyr Glu Lys Tyr Lys Lys Glu Asp Leu Asn Gln Lys Lys
 65                  70                  75                  80

Arg Leu Gln Gln Leu Leu Gln Arg Ala Leu Ile Asn Ser Gln Glu Leu
                 85                  90                  95

Gly Asp Glu Lys Ile Gln Ile Val Thr Gln Met Leu Glu Leu Val Glu
            100                 105                 110

Asn Arg Ala Arg Gln Met Glu Leu His Ser Gln Cys Phe Gln Asp Pro
            115                 120                 125

Ala Glu Ser Glu Arg Ala Ser Asp Lys Ala Lys Met Asp Ser Ser Gln
    130                 135                 140

Pro Glu Arg Ser Ser Arg Arg Pro Arg Arg Gln Arg Thr Ser Glu Ser
145                 150                 155                 160

Arg Asp Leu Cys His Met Ala Asn Gly Ile Glu Asp Cys Asp Asp Gln
                165                 170                 175

Pro Pro Lys Glu Lys Lys Ser Lys Ser Ala Lys Lys Lys Lys Arg Ser
            180                 185                 190

Lys Ala Lys Gln Glu Arg Glu Ala Ser Pro Val Glu Phe Ala Ile Asp
    195                 200                 205

Pro Asn Glu Pro Thr Tyr Cys Leu Cys Asn Gln Val Ser Tyr Gly Glu
    210                 215                 220

Met Ile Gly Cys Asp Asn Glu Gln Cys Pro Ile Glu Trp Phe His Phe
225                 230                 235                 240

Ser Cys Val Ser Leu Thr Tyr Lys Pro Lys Gly Lys Trp Tyr Cys Pro
                245                 250                 255

Lys Cys Arg Gly Asp Asn Glu Lys Thr Met Asp Lys Ser Thr Glu Lys
            260                 265                 270

Thr Lys Lys Asp Arg Arg Ser Arg
    275                 280

<210> SEQ ID NO 6
<211> LENGTH: 840
<212> TYPE: DNA
<213> ORGANISM: Homo sapiens
<220> FEATURE:
<223> OTHER INFORMATION: human embryonic brain cDNA library

<400> SEQUENCE: 6
atgttagggc agcagcagca gcaactgtac tcgtcggccg cgctcctgac c ggggagcgg      60 agccggctgc tcacctgcta cgtgcaggac taccttgagt gcgtggagtc g ctgccccac    120 gacatgcaga ggaacgtgtc tgtgctgcga gagctggaca caaatatca a gaaacgtta    180 aaggaaattg atgatgtcta cgaaaaatat aagaagaag atgatttaaa c cagaagaaa    240 cgtctacagc agcttctcca gagagcacta attaatagtc aagaattggg a gatgaaaaa    300 atacagattg ttacacaaat gctcgaattg gtggaaaatc gggcaagaca a atggagtta    360 cactcacagt gtttccaaga tcctgctgaa agtgaacgag cctcagataa a gcaagatg    420 gattccagcc aaccagaaag atcttcaaga agaccccgca ggcagcggac c agtgaaagc    480 cgtgatttat gtcacatggc aaatgggatt gaagactgtg atgatcagcc a cctaaagaa    540 aagaaatcca agtcagcaaa gaaaagaaa cgctccaagg ccaagcagga a agggaagct    600 tcacctgttg agtttgcaat agatcctaat gaacctacat actgcttatg c aaccaagtg    660 tcttatgggg agatgatagg atgtgacaat gaacagtgtc caattgaatg g tttcacttt    720 tcatgtgttt cacttaccta taaaccaaag gggaaatggt attgcccaaa g tgcagggga    780
```

```
gataatgaga aacaatgga caaaagtact gaaaagacaa aaaaggatag a agatcgagg      840

<210> SEQ ID NO 7
<211> LENGTH: 1078
<212> TYPE: DNA
<213> ORGANISM: Homo sapiens
<220> FEATURE:
<223> OTHER INFORMATION: human embryonic brain cDNA library
<221> NAME/KEY: CDS
<222> LOCATION: (92)..(931)

<400> SEQUENCE: 7
tccaagctga gctgagggcc cgcggcggcc gcggccggtg catgtgcggc t gctggatgc       60 ggaggcggcg gcgacggcgc ggatcggcag g atg tta ggg cag  cag cag cag        112
                                  Met Leu Gly Gln  Gln Gln Gln
                                   1               5 caa ctg tac tcg tcg gcc gcg ctc ctg acc g gg gag cgg agc cgg ctg       160
Gln Leu Tyr Ser Ser Ala Ala Leu Leu Thr G ly Glu Arg Ser Arg Leu
        10                  15                  20 ctc acc tgc tac gtg cag gac tac ctt gag t gc gtg gag tcg ctg ccc       208
Leu Thr Cys Tyr Val Gln Asp Tyr Leu Glu C ys Val Glu Ser Leu Pro
 25                  30                  35 cac gac atg cag agg aac gtg tct gtg ctg c ga gag ctg gac aac aaa       256
His Asp Met Gln Arg Asn Val Ser Val Leu A rg Glu Leu Asp Asn Lys
 40                  45                  50                  55 tat caa gaa acg tta aag gaa att gat gat g tc tac gaa aaa tat aag       304
Tyr Gln Glu Thr Leu Lys Glu Ile Asp Asp V al Tyr Glu Lys Tyr Lys
                 60                  65                  70 aaa gaa gat gat tta aac cag aag aaa cgt c ta cag cag ctt ctc cag       352
Lys Glu Asp Asp Leu Asn Gln Lys Lys Arg L eu Gln Gln Leu Leu Gln
             75                  80                  85 aga gca cta att aat agt caa gaa ttg gga g at gaa aaa ata cag att       400
Arg Ala Leu Ile Asn Ser Gln Glu Leu Gly A sp Glu Lys Ile Gln Ile
         90                  95                 100 gtt aca caa atg ctc gaa ttg gtg gaa aat c gg gca aga caa atg gag       448
Val Thr Gln Met Leu Glu Leu Val Glu Asn A rg Ala Arg Gln Met Glu
    105                 110                 115 tta cac tca cag tgt ttc caa gat cct gct g aa agt gaa cga gcc tca       496
Leu His Ser Gln Cys Phe Gln Asp Pro Ala G lu Ser Glu Arg Ala Ser
120                 125                 130                 135 gat aaa gca aag atg gat tcc agc caa cca g aa aga tct tca aga aga       544
Asp Lys Ala Lys Met Asp Ser Ser Gln Pro G lu Arg Ser Ser Arg Arg
                140                 145                 150 ccc cgc agg cag cgg acc agt gaa agc cgt g at tta tgt cac atg gca       592
Pro Arg Arg Gln Arg Thr Ser Glu Ser Arg A sp Leu Cys His Met Ala
            155                 160                 165 aat ggg att gaa gac tgt gat gat cag cca c ct aaa gaa aag aaa tcc       640
Asn Gly Ile Glu Asp Cys Asp Asp Gln Pro P ro Lys Glu Lys Lys Ser
        170                 175                 180 aag tca gca aag aaa aag aaa cgc tcc aag g cc aag cag gaa agg gaa       688
Lys Ser Ala Lys Lys Lys Lys Arg Ser Lys A la Lys Gln Glu Arg Glu
    185                 190                 195 gct tca cct gtt gag ttt gca ata gat cct a at gaa cct aca tac tgc       736
Ala Ser Pro Val Glu Phe Ala Ile Asp Pro A sn Glu Pro Thr Tyr Cys
200                 205                 210                 215 tta tgc aac caa gtg tct tat ggg gag atg a ta gga tgt gac aat gaa       784
Leu Cys Asn Gln Val Ser Tyr Gly Glu Met I le Gly Cys Asp Asn Glu
                220                 225                 230 cag tgt cca att gaa tgg ttt cac ttt tca t gt gtt tca ctt acc tat       832
Gln Cys Pro Ile Glu Trp Phe His Phe Ser C ys Val Ser Leu Thr Tyr
```

-continued

```
                   235                 240                 245
aaa cca aag ggg aaa tgg tat tgc cca aag t gc agg gga gat aat gag      880
Lys Pro Lys Gly Lys Trp Tyr Cys Pro Lys C ys Arg Gly Asp Asn Glu
        250                 255                 260 aaa aca atg gac aaa agt act gaa aag aca a aa aag gat aga aga tcg      928
Lys Thr Met Asp Lys Ser Thr Glu Lys Thr L ys Lys Asp Arg Arg Ser
    265                 270                 275 agg tagtaaggc catccacatt ttaaagggtt atttgactat tatataat cc            981
Arg
280 gtttgctttc agaaaatgtt ttagggtaaa tgcataagac tatgcaataa t tattaatca   1041 ttagtattaa tggtgtatta aaagttgttg tactttg                             1078

<210> SEQ ID NO 8
<211> LENGTH: 280
<212> TYPE: PRT
<213> ORGANISM: Homo sapiens
<223> OTHER INFORMATION: human embryonic brain cDNA library

<400> SEQUENCE: 8

Met Leu Gly Gln Gln Gln Gln Leu Tyr S er Ser Ala Ala Leu Leu
 1               5                  10                  15

Thr Gly Glu Arg Ser Arg Leu Leu Thr Cys T yr Val Gln Asp Tyr Leu
            20                  25                  30

Glu Cys Val Glu Ser Leu Pro His Asp Met G ln Arg Asn Val Ser Val
        35                  40                  45

Leu Arg Glu Leu Asp Asn Lys Tyr Gln Glu T hr Leu Lys Glu Ile Asp
    50                  55                  60

Asp Val Tyr Glu Lys Tyr Lys Glu Asp A sp Leu Asn Gln Lys Lys
 65                  70                  75                  80

Arg Leu Gln Gln Leu Leu Gln Arg Ala Leu I le Asn Ser Gln Glu Leu
                85                  90                  95

Gly Asp Glu Lys Ile Gln Ile Val Thr Gln M et Leu Glu Leu Val Glu
            100                 105                 110

Asn Arg Ala Arg Gln Met Glu Leu His Ser G ln Cys Phe Gln Asp Pro
        115                 120                 125

Ala Glu Ser Glu Arg Ala Ser Asp Lys Ala L ys Met Asp Ser Ser Gln
    130                 135                 140

Pro Glu Arg Ser Ser Arg Arg Pro Arg Arg G ln Arg Thr Ser Glu Ser
145                 150                 155                 160

Arg Asp Leu Cys His Met Ala Asn Gly Ile G lu Asp Cys Asp Asp Gln
                165                 170                 175

Pro Pro Lys Glu Lys Ser Lys Ser Ala L ys Lys Lys Arg Ser
            180                 185                 190

Lys Ala Lys Gln Glu Arg Glu Ala Ser Pro V al Glu Phe Ala Ile Asp
        195                 200                 205

Pro Asn Glu Pro Thr Tyr Cys Leu Cys Asn G ln Val Ser Tyr Gly Glu
    210                 215                 220

Met Ile Gly Cys Asp Asn Glu Gln Cys Pro I le Glu Trp Phe His Phe
225                 230                 235                 240

Ser Cys Val Ser Leu Thr Tyr Lys Pro Lys G ly Lys Trp Tyr Cys Pro
                245                 250                 255

Lys Cys Arg Gly Asp Asn Glu Lys Thr Met A sp Lys Ser Thr Glu Lys
            260                 265                 270

Thr Lys Lys Asp Arg Arg Ser Arg
```

```
                      275                280
```

```
<210> SEQ ID NO 9
<211> LENGTH: 10
<212> TYPE: DNA
<213> ORGANISM: Artificial Sequence
<220> FEATURE:
<223> OTHER INFORMATION: Description of Artificial  Sequence: PCR primer
      sequence for TSC403

<400> SEQUENCE: 9
gatctgacac                                                              10

<210> SEQ ID NO 10
<211> LENGTH: 28
<212> TYPE: DNA
<213> ORGANISM: Artificial Sequence
<220> FEATURE:
<223> OTHER INFORMATION: Description of Artificial  Sequence: PCR primer
      P1

<400> SEQUENCE: 10
gatcggatcc aggaggatgc gggtccgg                                          28

<210> SEQ ID NO 11
<211> LENGTH: 30
<212> TYPE: DNA
<213> ORGANISM: Artificial Sequence
<220> FEATURE:
<223> OTHER INFORMATION: Description of Artificial  Sequence: PCR primer
      P2

<400> SEQUENCE: 11
gatcctcgag ttactgtggt ggctgctgct                                        30
```